US009549997B2

(12) United States Patent
Walton et al.

(10) Patent No.: US 9,549,997 B2
(45) Date of Patent: Jan. 24, 2017

(54) OPTICAL IMAGING PROBES

(75) Inventors: Tashfeen Walton, Edinburgh (GB); Mark Bradley, Edinburgh (GB); Kev Dhaliwal, Edinburgh (GB); Nikolaos Avlonitis, Edinburgh (GB); Chris Haslett, Edinburgh (GB); Neil McDonald, Edinburgh (GB); Manuelle Debunne, Edinburgh (GB)

(73) Assignee: THE UNIVERSITY COURT OF THE UNIVERSITY OF EDINBURGH, Edinburgh (GB)

( * ) Notice: Subject to any disclaimer, the term of this patent is extended or adjusted under 35 U.S.C. 154(b) by 413 days.

(21) Appl. No.: 14/110,616

(22) PCT Filed: Apr. 5, 2012

(86) PCT No.: PCT/GB2012/000314
§ 371 (c)(1),
(2), (4) Date: Jan. 27, 2014

(87) PCT Pub. No.: WO2012/136958
PCT Pub. Date: Oct. 11, 2012

(65) Prior Publication Data
US 2014/0134110 A1 May 15, 2014

(30) Foreign Application Priority Data
Apr. 8, 2011 (GB) .................................. 1106004.3

(51) Int. Cl.
A61B 10/00 (2006.01)
A61B 5/00 (2006.01)
A61B 8/00 (2006.01)
A61K 49/00 (2006.01)
G01N 21/64 (2006.01)

(52) U.S. Cl.
CPC ......... *A61K 49/006* (2013.01); *A61K 49/0041* (2013.01); *A61K 49/0054* (2013.01); *A61K 49/0056* (2013.01); *G01N 21/6458* (2013.01); *G01N 2021/6432* (2013.01); *G01N 2021/6441* (2013.01)

(58) Field of Classification Search
CPC .. A61K 49/00; A61K 49/006; A61K 49/0041; A61K 49/0054; A61K 49/0056; G01N 21/6458; G01N 2021/6432; G01N 2021/6441
USPC .... 424/1.11, 1.65, 1.69, 1.81, 1.89, 9.1, 9.2, 424/9.6
See application file for complete search history.

(56) References Cited

U.S. PATENT DOCUMENTS

| 5,527,524 A | 6/1996 | Tomalia et al. |
| 8,568,693 B2* | 10/2013 | Danikas et al. ............... 424/9.2 |
| 2010/0278745 A1* | 11/2010 | Lange ................ A61K 49/0021 424/9.6 |
| 2011/0065896 A1 | 3/2011 | Licha et al. |

FOREIGN PATENT DOCUMENTS

| WO | WO 03/014743 | 2/2003 |
| WO | WO 03/101474 | 11/2003 |
| WO | WO 2007/109364 | 9/2007 |
| WO | WO 2008/020130 | 2/2008 |

OTHER PUBLICATIONS

Shi et al, Biomacromolecules, 2009, vol. 10, pp. 1744-1750.*
Abu-Amara et al., "Liver Ischemia/Reperfusion Injury: Processes in Inflammatory Networks—A Review", Liver Transp. (2010) vol. 16, pp. 1016-1032.
Albertazzi et al., "Dendrimer Internalization and Intracellular Trafficking in Living Cells", Molecular Pharmaceutics (2010) vol. 7, No. 3, 680-688. Reference provides "Published on Web Apr. 15, 2010", the contents of which have not been verified by the undersigned.
Astruc et al., "Dendrimers Designed for Functions; From Physical, Photophysical, and Supramolecular Properties to Applications in Sensing, Catalysis, Molecular Electronics, Photonics, and Nanomedicine", Chem. Rev. (2010) vol. 110, No. 4, pp. 1857-1959. Reference provides "Published on Web Mar. 31, 2010", the contents of which have not been verified by the undersigned.
Balamayooran et al., "Mechanism of Neutrophil Accumulation in the Lungs Against Bacteria", Am. J. Resp. Cell Mol. Biol. (2010) vol. 43, pp. 5-16. Reference provides "Originally Published in Press as DOI:10.1165/RCMB.2009-0047tr on Sep. 8, 2009", the contents of which have not been verified by the undersigned.
Biricova et al., "Dendrimers: Analytical Characterization and Applications", Bioorganic Chem. (2009), vol. 37, pp. 185-192. Reference provides "Available online Aug. 3, 2009", the contents of which have not been verified by the undersigned.
Brouwer et al., Convergent Synthesis and Diversity of Amino Acid Based Dendrimers, Eur. J. Org. Chem. (2001), pp. 1903-1915.

(Continued)

*Primary Examiner* — D L Jones
(74) *Attorney, Agent, or Firm* — Hoxie & Associates LLC

(57) ABSTRACT

The present invention relates to methods of visualizing cells especially although not exclusively in vivo using a dye, such as a dendrimer-dye molecule or polybranched-dye molecule which is internalized by the cells and thus permits subsequent visualization by confocal fluorescence endomicroscopy or other optical detectors. There is also provided internally quenched probes for use in visualizing cells especially although not exclusively in vivo by confocal fluorescence endomicroscopy and the use of internally quenched probes in combination with confocal fluorescence endomicroscopy, for visualizing cells by virtue of internalization and dequenching of a probe by the cells. In a particular embodiment the cells are activated neutrophils, such as within the lung of a subject.

13 Claims, 15 Drawing Sheets

(56) References Cited

OTHER PUBLICATIONS

Chen et al.,"Positron Emission Tomography with [$^{18}$F]Fluorodeoxyglucose to Evaluate Neutrophil Kinetics During Acute Lung Injury", Am. J. Physiol. Lung Cell Mol. Physiol. (2004) vol. 286 pp. L834-L840. Reference provides "First published Dec. 5, 2003; 10.1152/ajplung.00339.2003.", the contents of which have not been verified by the undersigned.
Chua et al., "Neutrophil Elastase Mediator of Extracellular Matrix Destruction and Accumulation", Proc. Am. Thorac Soc. (2006) vol. 3, pp. 424-427.
Collie et al., "Local Lung Responses Following Local Lung Challenge With Recombinant Lungworm Antigen in Systemically Sensitized Sheep", Clinical and Exp. Allergy (2001) vol. 31 , pp. 1636-1647.
Conway Morris et al., "C5a Mediates Peripheral Blood Neutrophil Dysfunction in Critically Ill Patients", Am. J. Respir. Crit. Care Med. (2009) vol. 180, pp. 19-28. Reference provides "Originally Published in Press as DOI:10.1164/rccm.200812-1928OC on Mar. 26, 2009", the contents of which have not been verified by the undersigned.
Demkow et al., "Role of Elastases in the Pathogenesis of Chronic Obstructive Pulmonary Disease: Implications for Treatment", Eur. J. Med. Res. (2010), vol. 15(Suppl. II), pp. 27-29.
Demmer et al., "Introduction of Functional Groups Into Peptides via N-Alkylation", Organic Letters (2008) vol. 10, No. 10, pp. 2015-2018. Reference provides "Published on Web Apr. 12, 2008", the contents of which have not been verified by the undersigned.
den Hengst et al., "Lung Ischemia-Reperfusion Injury: A Molecular and Clinical View on a Complex Pathophysiological Process", Am. J. Physiol. Heart Circ. Physiol. (2010) vol. 299, pp. 1283-1299. Reference provides "First published Sep. 10, 2010; doi:10.1152/ajpheart.00251.2010", the contents of which have not been verified by the undersigned.
Donnelly et al., "Plasma Elastase Levels and the Development of the Adult Respiratory Distress Syndrome", Am. J. Respir. Crit. Care Med. (1995) vol. 151, pp. 1428-1433.
Downey et al., "Neutrophils in Cystic Fibrosis", Thorax (2009) vol. 64, pp. 81-88.
Ellard et al., "Fluorescence Enhancement Through Enzymatic Cleavage of Internally Quenched Dendritic Peptide: A Sensitive Assay for the AspN Endoproteinase", Angew. Chem. (2002) vol. 114, No. 17, pp. 3367-3370.
Fischer et al., "Extending The Applicability of Carboxyfluorescein in Solid-Phase Synthesis", Bioconjugate Chem. (2003) vol. 14, pp. 653-660. Reference provides "Published on Web Apr. 30, 2003", the contents of which have not been verified by the undersigned.
Galande et al.,"Enzyme-Targeted Fluorescent Imaging Probes on a Multiple Antigenic Peptide Core" J Med. Chem. (2006), vol. 49, pp. 4715-4720. Reference provides "Published on Web Jul. 1, 2006", the contents of which have not been verified by the undersigned.
PerkinElmer Catalog—Product Info Page—Product ID—NEV11169; available at: http://las.perkinelmer.com/Catalog/ProductInfoPage.htm?ProductID=NEV11169. Copyright 2010.
Kaiser et al., "Color Test for Detection of Free Terminal Amino Groups in the Solid-Phase Synthesis of Peptides", Analytical Biochemistry (1970) vol. 34, pp. 595-598.
Knolker et al., "A Novel Method for the Synthesis of Isocyanates Under Mild Conditions" Angew. Chem. Int. Ed. Engl. (1995) vol. 34, pp. 2497-2500.
Lebreton et al., "Solid-phase Construction: High Efficiency Dendrimer Synthesis using ABs Isocyanate-type Monomers", Tetrahedron (2003) vol. 59, pp. 3945-3953.
Najlah et al., "Crossing Cellular Barriers Using Dendrimer Nanotechnologies", Curr. Opin. Pharmacol. (2006), vol. 6, pp. 522-527. Reference provides "Available online Aug. 4, 2006", the contents of which have not been verified by the undersigned.
Pentz et al., "A Variable Cell Culture Chamber for 'open' and 'closed' Cultivation, Perfusion and High Microscopic Resolution of Living Cells", Journal of Microscopy (1992) vol. 167, pp. 97-103.
Shapiro S.D, "Neutrophil Elastase Path Clearer, Pathogen Killer, or Just Pathologic?" Am. J. Resp. Cell Mol. Biol. (2002) vol. 26, pp. 266-268.
Simpson et al., "Adenoviral Augmentation of Elafin Protects the Lung Against Acute Injury Mediated by Activated Neutrophils and Bacterial Infection", J. Immunol. (2001) vol. 167, pp. 1778-1786.
Ternon et al., "Dendrimers and Combinatorial Chemistry—Tools for Fluorescent Enhancement in Protease Assays", Tetrahedron (2004) vol. 60, pp. 8721-8728.
Thiberville et al., "In Vivo Imaging of the Bronchial Wall Microstructure Using Fibered Confocal Fluorescence Microscopy", Am J Respir Crit Care Med. (2007), vol. 175, pp. 22-31. Reference provides "Originally Published in Press as DOI: 10.1164/rccm.200605-684OC on Oct. 5, 2006", the contents of which have not been verified by the undersigned.
Thiberville et al., "Human in Vivo Fluorescence Microimaging Of The Alveolar Ducts and Sacs During Bronchoscopy", Eur. Respir. J. (2009) vol. 33, pp. 974-985.
Thiberville et al., "Confocal Fluorescence Endomicroscopy of the Human Airways", Proc. Am. Thorac Soc. (2009) vol. 6, pp. 444-449.
Tsushima et al.,"Acute Lung Injury Review", Inter Med. , (2009), vol. 48, pp. 621-630.

* cited by examiner

Chemical structures

Figure 4 Chemical structures (Amino acids; L or D)

OPTICAL IMAGING PROBES

FIELD OF INVENTION

The present invention relates to methods of visualising cells especially although not exclusively in vivo using a dye, such as a dendrimer-dye molecule or polybranched-dye molecule which is internalised by the cells and thus permits subsequent visualisation by confocal fluorescence endomicroscopy or other optical detectors. There is also provided internally quenched probes for use in visualising cells especially although not exclusively in vivo by confocal fluorescence endomicroscopy and the use of internally quenched probes in combination with confocal fluorescence endomicroscopy, for visualising cells by virtue of internalisation and dequenching of a probe by the cells. In a particular embodiment the cells are activated neutrophils, such as within the lung of a subject.

BACKGROUND OF THE INVENTION

Neutrophil predominant lung inflammation is a major cause of morbidity and mortality[11]. Yet despite decades of investigation, accurate stratification of patients with neutrophil predominant lung injury on intensive care has been hindered by the lack of bedside point of care diagnostics that can reliably and rapidly distinguish acute neutrophilic inflammation[2]. The ability to perform bedside diagnostics has the potential to accurately stratify such patients for further neutrophil specific interventions. Excessive neutrophil activity degrades matrix and cellular receptors, activates profibrogenic mediators and contributes to epithelial and endothelial cell damage[3,4,5]. The involvement of neutrophils in several diseases such as acute lung injury, ischemia-reperfusion injury[6,7], cystic fibrosis[8] and chronic obstructive pulmonary disease, makes them important targets for modulation.

In situ in vivo detection of neutrophilic inflammation in human pulmonary inflammation has been reliant upon FDG PET imaging. PET imagine[10], although offering exquisite sensitivity, is cumbersome, expensive and is difficult to implement as a bedside molecular imaging modality. Conversely the advent of confocal endoscopy, such as probe based confocal laser endoscopy has revolutionised the ability to directly visualise the alveolar space in both preclinical and clinical arenas. However, as yet this modality has only been used to image autofluorescent structures within the alveolar space or using non-specific fluorescent dyes[11,12].

The optical detection of activated neutrophilic activity is feasible with imaging enzymatic activity in whole animals[13]. These approaches require substrate specificity with internally quenched molecular beacons. Often the dequenching may take hours and the substrate may be cleaved by non neutrophil proteases.

Dendrimers are a class of macromolecules possessing a well-defined structure and molecular composition[14,15].

They are created by the stepwise attachment of monomer units in repeating unit layers, termed generations, which creates branches built upon a central core. These branches terminate in a specific chemical functional group that can be used for further dendrimer growth or modification, or attachment of specific compounds as required.

WO2003014743 describes the use of dendrimers and polybranched molecules to enhance signals in in vitro fluorescent assay systems[16].

The molecules disclosed in WO2003014743 comprise cleavage sites which when treated with an appropriate chemical or enzyme lead to cleavage of selective bonds within the molecules and a subsequent change in the fluorescent properties of the molecule, most notably an increase in fluorescence. However, WO2003014743 only shows the results of in vitro data and there is no suggestion or teaching of how one might use the molecules in an in vivo setting, or indeed if this would in fact be possible.

It is an object of the present invention to obviate and/or mitigate at least one of the aforementioned disadvantages.

It is an object of the present invention to provide means of visualising cells in vivo, such as activated neutrophils within the lung of a subject, using confocal microendoscopy.

In a first aspect there is provided a dye construct which prior to cell internalisation displays substantially no detectable or only a low amount of fluorescence, but upon cell internalisation displays a detectable increase in fluorescence using confocal endoscopy for use in imaging cells in vivo.

The dye construct may be a poly-branched molecule with surface groups linked to a fluorescent dye, such as disclosed in WO/2003/014743, or a molecule as further described herein.

"Detectable increase in fluorescence" is understood to relate to fluorescence which can be detected by confocal microendoscopy techniques. If the dye constructs initially display a low, but detectable level of fluorescence, then a detectable increase can be observed following internalisation by a cell or cells. Initially the dye constructs for use in the present invention are internally quenched. That is, the dye constructs do not fluoresce or fluoresce poorly due to the fluorescent groups or groups being quenched. However, following internalisation by cells, dequenching occurs and an increase in fluorescence can be detected.

Typically fluorescence detection is understood to be related to fluorescence intensity, fluorescence lifetime and polarisation may also be detected. Typically the "low or little" amount of fluorescence" is practically not detectable using confocal microendoscopy techniques, or is sufficiently low to permit a clear identification of the "increase" in fluorescence. Typically a suitable increase is understood to be an increase by a factor of 1.2 or more.

The present inventors have observed that combining confocal endoscopic visualisation techniques with the localised administration of a dendrimer dye molecule or poly-branched molecule linked fluorescent dye, it is possible to observe in vivo, by way of fluorescence, specific cells which internalise a dye construct of the present invention or poly-branched molecule linked fluorescent dye, with a distinct increase in fluorescence. Without wishing to be bound by theory, it is thought that the dye contructs/polybranched-dye molecules of the present invention are internalised or taken up by cells before internal cellular mechanisms act upon the constructs causing an increase in fluorescence.

The present inventors have observed that through the use of the dye construct/poly-branched molecules described herein, that such molecules are capable of being internalised, by certain specific cells within seconds or a few minutes. However, over time many different cell types may internalise the dye construct/poly-branched molecules described herein and as such, in order to observe the desired cells which rapidly internalise the dye construct/poly-branched molecules described herein, the detection of fluorescence should be carried out within a few minutes of administering the dye construct—typically within seconds to minutes, such as 1-30 minutes, typically 1-10 minutes. In this manner, cells which may internalise such constructs over a much longer time period, such as within hours, are not detected and hence the cells which rapidly internalise the dye constructs are readily discernable, from other cells. This is also advantageous to the patient, as they are subjected to the diagnostic procedure for as short a time as possible. Moreover, if the endoscope were removed, the site of administration of the dye construct may be difficult to relocate.

The confocal endoscope or microendoscope enables real-time in vivo human and animal imaging. The instrument couples a custom built fluorescence slit-scan confocal microscope to a fibre-optic catheter. Further teaching may be found in Thiberville et al[17] and WO2008020130, to which the skilled reader is directed and the contents of which are hereby incorporated by way of reference.

In a further aspect there is provided a method of visualising a particular cell or cells within a mixture of cells in vivo using confocal endomicroscopy, comprising the step of adding a dye construct or poly-branched molecule linked fluorescent dye to said mixture of cells and observing a cell or cells which have internalised the dye construct or poly-branched molecule linked fluorescent dye by observing fluorescence from said cell or cells using a confocal fluorescence endomicroscope. Conveniently the dye construct or poly-branched molecule linked fluorescent dye may be one of the constructs described herein.

Typically the cells which may be detected by way of internalising the dye construct or poly-branched molecule linked fluorescent dye are activated neutrophils. Activated neutrophils which are characterised by degranulation and protease release may be found at sites of inflammation and may therefore be detected using confocal endoscopy techniques at a variety of locations within the body of a subject such as within in the lung, within the gastrointestinal tract, within the reproductive tract or any other endoscopically accessible orifice.

In a preferred embodiment activated neutrophils are detected in the lung of a subject. Typically the subject may be a subject already hospitalised, such as a patient in intensive care, where early detection of such activated neutrophils would be desirable.

The dye construct or poly-branched molecule linked to fluorescent dye may be of the form described in, for example, WO/2003/014743 (to which the skilled reader is directed and the entire contents of which are incorporated herein, by way of reference) which comprise one or more cleavage sites which are cleavable by appropriate chemical or enzyme means. Preferred molecules comprise three or more, typically six or more branches, such that a significant increase in fluorescence may be observed following dequenching of the fluorescent moieties.

In addition to the molecules described in WO2003/014743, preferred poly-branched molecules of the present invention have the generalised structures as follows:

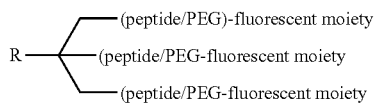

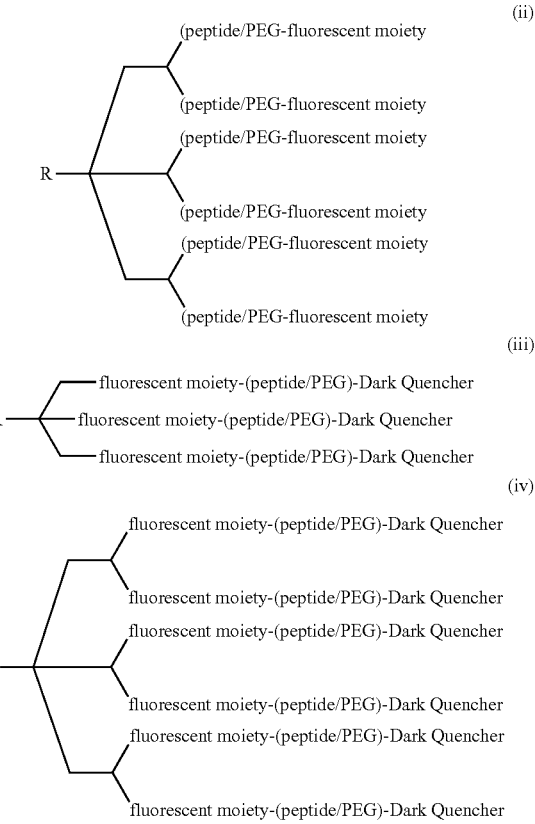

Where R is selected from $NH_2$, $CONH_2$, $NH_2CONH$—, an amino acid, OH, amino acid —$CONH_2$, $CONH_2$—amino acid, alkylamino, alkoxyamino, urea, thiol, carboxylic acid, or a further fluorophore moiety which may be the same or different to the other fluorescent moieties. All such groups may be directly attached to the branch point, or may be separated from the branch point by a spacer, which may be a PEG group, an alkyl or alkenyl chain, such as a $C_1$-$C_{10}$ alkyl or alkenyl. Other linking groups are described in WO2003/014743 and reference 14.

The above generalised structures schematically represent probes which may be suitable for use in the present invention. The use of a peptide and/or polyethylene glycol (PEG) portion is intended to improve the solubility of the dendrimer/branched molecules. When present the peptide sequence may comprise an enzyme or chemical cleavage recognition sequence or may be random in the sense of not including a recognisable enzyme or chemical cleavage recognition sequence. As an alternative to the peptide and/or PEG moiety, any suitable solubilising group known in the art may be used. Without wishing to be bound by theory, when a random peptide sequence is employed, the peptide sequence is not thought to be cleaved by an enzyme present in the cell to be detected. Thus, the increase in fluorescence observed following internalisation of the molecules of the present invention comprising random peptide sequences is not thought to be due to cleavage of the peptide moiety and release of previously quenched fluorescent moieties, in contrast to previous teachings.

When an enzyme cleavable sequence is employed, the peptide sequence may be cleaved by an enzyme which may be present outside of the cell and this may result in a low amount of fluorescence being observed. However, a far greater observable increase in fluorescence is observed upon internalisation of the molecules/probes. In this manner the separation of the dequencher moiety from the fluorescent moiety, as well as other cellular mechanisms results in a significant increase in fluorescence being observed. Thus, in an embodiment where a degree of fluorescence may be observed outside of the cell it is to be understood that a detectable increase is observed (such as greater than a factor of 1.2 as compared to any fluorescence which is observed outside of the cell) when the construct in internalised. This may in fact be an advantage, as it may allow cells to be generally identified by way of a level of fluorescence being observed outside any cells, but desired cells can more easily be identified once the constructs are internalised and an increase in fluorescence observed.

Particularly preferred molecules of the present invention are selected from one of the following structures:

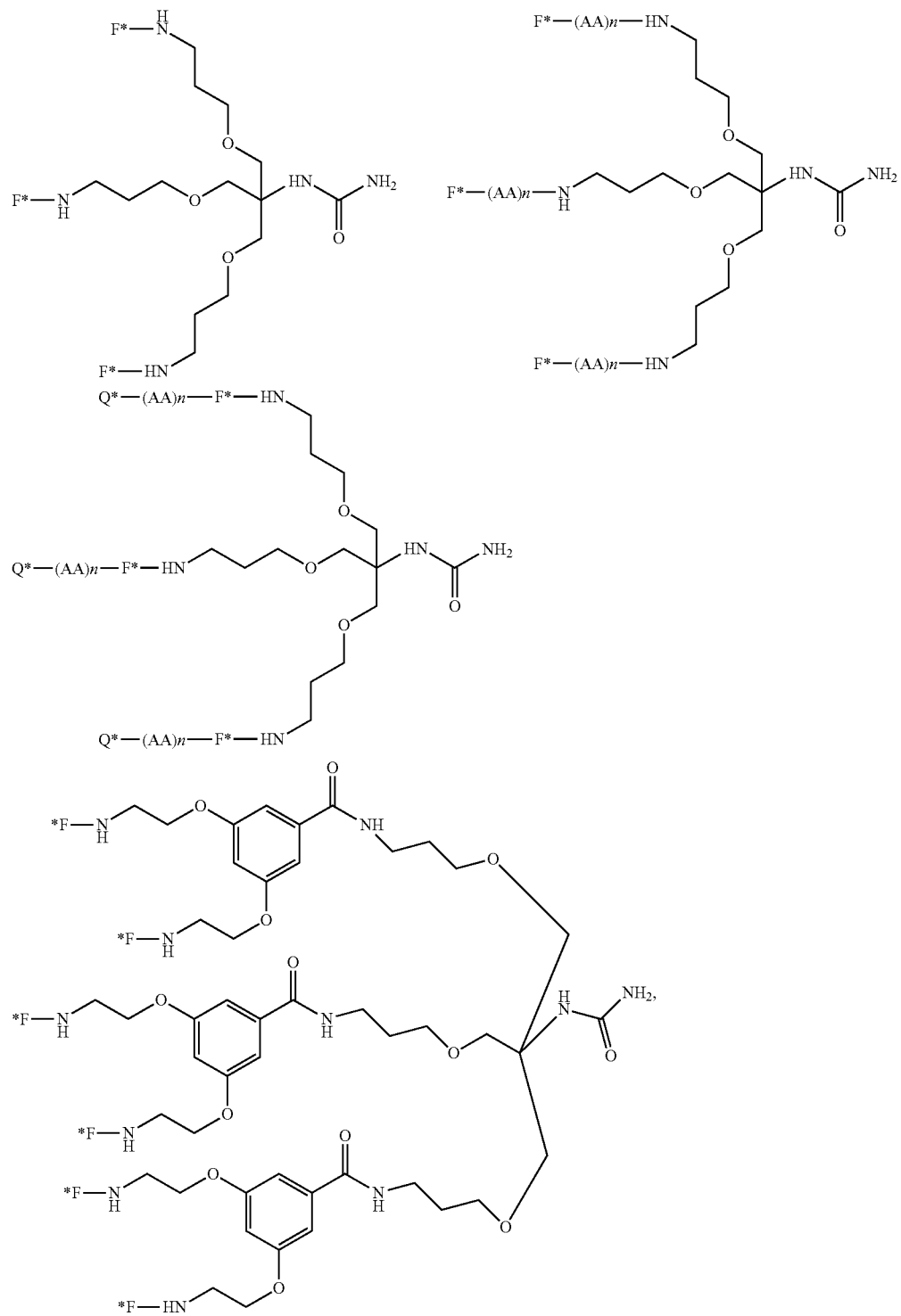

-continued

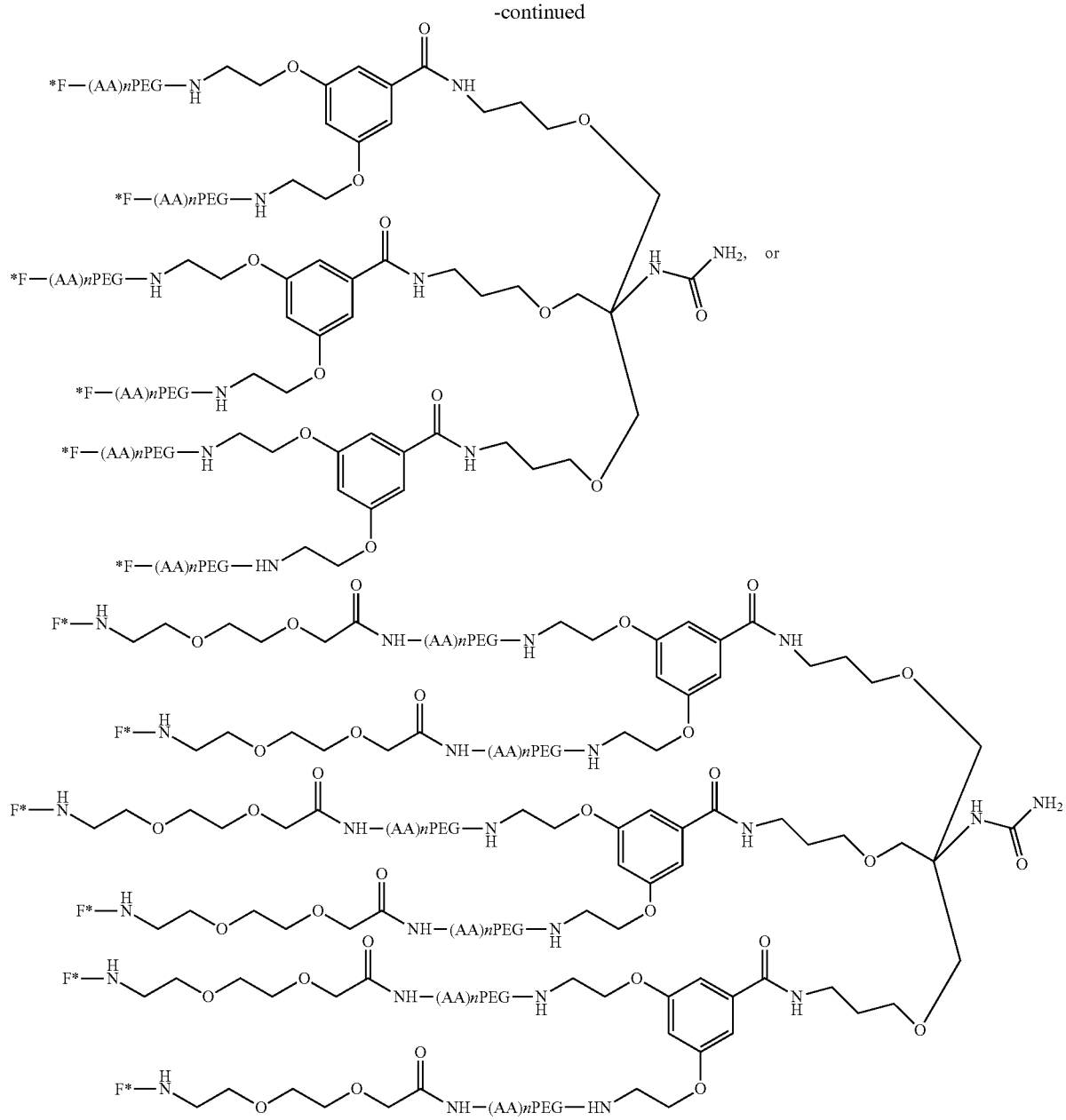

(AA)nPEG is to be understood as a peptide and/or PEG moiety being present. That is one or the other or both. Indeed more than one PEG may be present. The above molecules comprise a plurality of fluorescently quenched moieties, designated *F. One such fluorescent moiety is FAM, but it is to be understood that the molecules of the present invention are not limited to the use of FAM as many other fluorescent moieties may be used, such as rhodamine, cyanine dyes and BODIPY dyes. Q* is a dark quencher moiety such as DABCYL, Methyl Red, BHQ1, BHQ2 and BHQ3.

The molecules of the present invention may comprise a peptide linkage, represented in the above structures as (AA)n, where AA means any amino acid and n may be zero or is a positive integer from 1-30 such as 1-20, or 1-15. Such peptide sequences may therefore be random sequences, or conform to known sequences contained within peptides or proteins. Sequences which are recognised by the enzyme neutrophil elastase include A-A-P-V, A-A-A-P-V-K, E-E-I-Nle-R-R. Many other peptide sequences are known to the skilled addressee and may be used in probes of the present invention, examples include G-P-K-G-L-K-G (for MMP-9), V-A-D-C-A-D-Y (for proteinase 3), A-A-P-F, or F-V-T-Gnf-S-W where Gnf=nonproteinogenic 4-guanidine-1-phenylalanine) (for cathepsin G) and D-C-V-D (for Caspase). In a further aspect, the present invention provides novel dye constructs as described above for use in visualising cells, such as activated neutrophils, in vivo. There is also provided methods of preparing such molecules as described hereinafter.

The molecules of the present invention and indeed molecules described in WO/2003/014743 are initially quenched, that is they display little or no fluorescence in terms of fluorescence which may be detected from the fluorescent moiety following appropriate excitation. However, following internalisation of the molecules by the cell or cells to be detected, a de-quenching of the molecules occurs and an increase in fluorescent signal, following excitation using light of a suitable wavelength, can be detected[18].

Additionally, the present inventors have observed that certain molecules of the present invention which do not have recognisably cleavable peptide sequences are nevertheless internalised by certain cells, such as activated neutrophils and a de-quenching i.e. increase in fluorescence can be observed. Without wishing to be bound by theory, it is thought that the probes may be internalised into acidified vacuolar structures that directly effect internal quenching efficiency.

Thus, in a manner different to that described, for example, by WO2003014743, the molecules of the present invention do not necessarily have to possess recognisable enzyme cleavable peptide sequences in order to visualise cells and in particular activated neutrophils.

The present inventors are able through confocal endoscopy to visualise cells in situ in vivo. As such the term "in vivo" is to be understood to relate to cells within the living body and hence is to be distinguished from visualising cells obtained from tissue samples which have been extracted or excised from the body. The present methods may be conducted on or within any organ into which an endomicroscopic catheter may be inserted. This may be, for example, the gut including the large and small intestine; arteries and veins; the respiratory system including the lungs, the brain such as via an intracranial catheter; and the reproductive system including the womb and fallopian tubes.

In a particularly preferred embodiment, the methods of the present invention may be carried out whilst visualising cells in the lung, such as in the alveolar space.

The present inventors have observed that through the use of the dye constructs/poly-branched molecules described herein, that such molecules are capable of being internalised, by activated neutrophils. Such internalisation by activated neutrophils occurs very rapidly, within a few seconds or minutes and as such activated neutrophils may be visualised within 1-30 minutes, typically 1-10 minutes of the molecules of the present invention being administered to the subject at the site of investigation, such as within the lung. As mentioned above, the methods of detection as described herein should typically be conducted within a short period of time, following local administration of the initially quenched molecules, typically within a few minutes of administration, so that only cells, such as activated neutrophils, which internalise or take up the molecules of the present invention rapidly, are detected. Other cell types may also internalise the molecules, but over a much longer period of time. Thus, following the techniques of the present invention, it is possible to rapidly detect activated neutrophils in a mixed population of cells. In a particularly preferred embodiment, it is possible to detect activated neutrophils within the lung, such as in the alveolar space, of a subject.

Moreover, due to the sensitivity and increase in fluorescence following dequenching of the fluorescent moieties, it is possible to detect fluorescence from only microdosed amounts (typically less than 100 μg) such as less than 50 μg or even 10 μg or less of the dye construct which has been administered. This is particularly advantageous in terms of certain possible regulatory issues concerning the use of larger quantities and toxicity concerns when administering any exogenous molecule—although the molecules of the present invention may not in fact be significantly toxic in any case. It is in fact particularly surprising that such low microdose amounts of molecule when administered are capable of eliciting a signal which is detectable using microendoscopy techniques.

Thus, in a further embodiment, the present invention provides a method of visualising a particular cell or cells (such as activated neutrophils) within a mixture of cells in vivo using confocal endomicroscopy, comprising the step of adding a microdose (i.e. less than 100 μg, 50 μg, or 10 μg or less) of a dye construct or poly-branched molecule linked fluorescent dye to said mixture of cells and observing a cell or cells which have internalised the dendrimer dye molecule or poly-branched molecule linked fluorescent dye by observing fluorescence from said cell or cells using a confocal endomicroscope.

The present invention also provides use of a dendrimer dye molecule or poly-branched molecule linked fluorescent dye of the present invention in an amount of less than 100 μg, 50 μg, or 10 μg or less, for visualising cells in vivo using confocal endoscopy.

There is also provided a catheter or other suitable administration device comprising a microdose (i.e. less than 100 μg, 50 μg, or 10 μg or less) amount of a dye construct or poly-branched molecule linked fluorescent dye of the present invention, for administration to a subject, such that a cell or cells is capable of being visualised by confocal endoscopy.

One potential advantage of the present invention is that it may be carried out on subjects who are being given respiratory support in terms of being administered oxygen or air and who as such may have a face mask covering their mouth and/or nose or who are being intubated. Even in such a situation, it is possible to insert a confocal microendoscopy catheter into the lungs through the nasal passage or via the endotracheal tube. In this manner the present invention can truly be carried out at the bedside, without necessarily having to move the subject unduly. Moreover, for such subjects, the ability to detect any activated neutrophils, which are a key marker of an inflammatory response is of paramount importance and as such the present invention may find particular use in being conducted on such ill patients where moving them to another location may be undesirable and/or problematic.

BRIEF DESCRIPTION OF THE DRAWINGS

The present invention will now be further described by way of example and with reference to the following figures which show.

Figure 2:
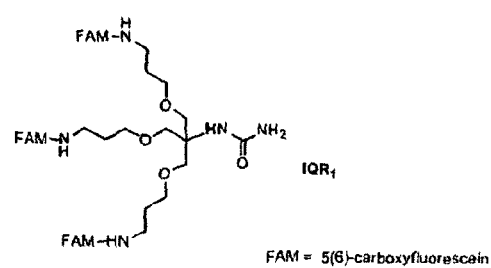
Figure 2:
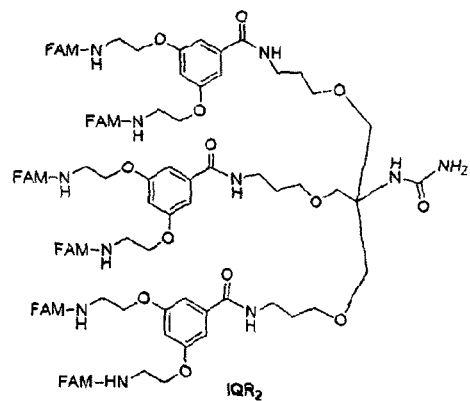
Figure 2:
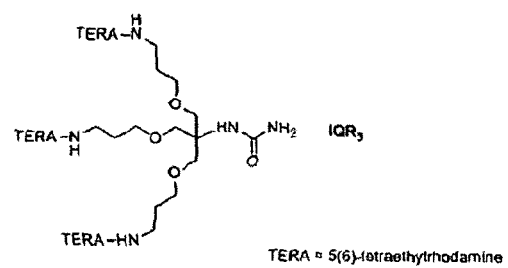

A) Activation of freshly isolated human neutrophils (PMNs) with 10 μM A23187 (calcium ionophore) leads to rapid appearance of punctate cell-associated fluorescence (imaged at 15 min post stimulation); B) This uptake of FAM is prevented by pretreatment with the dynamin inhibitor Dynasore; and C) Cell specificity: PMNs (white arrow), monocytes (open arrow) and lymphocytes (arrows head). Only activated PMN's internalise FAM. Cells are delineated by Syto-85 nuclear dye (red);

FIG. 2 shows the structure of some dendrimers.

Figure 3:
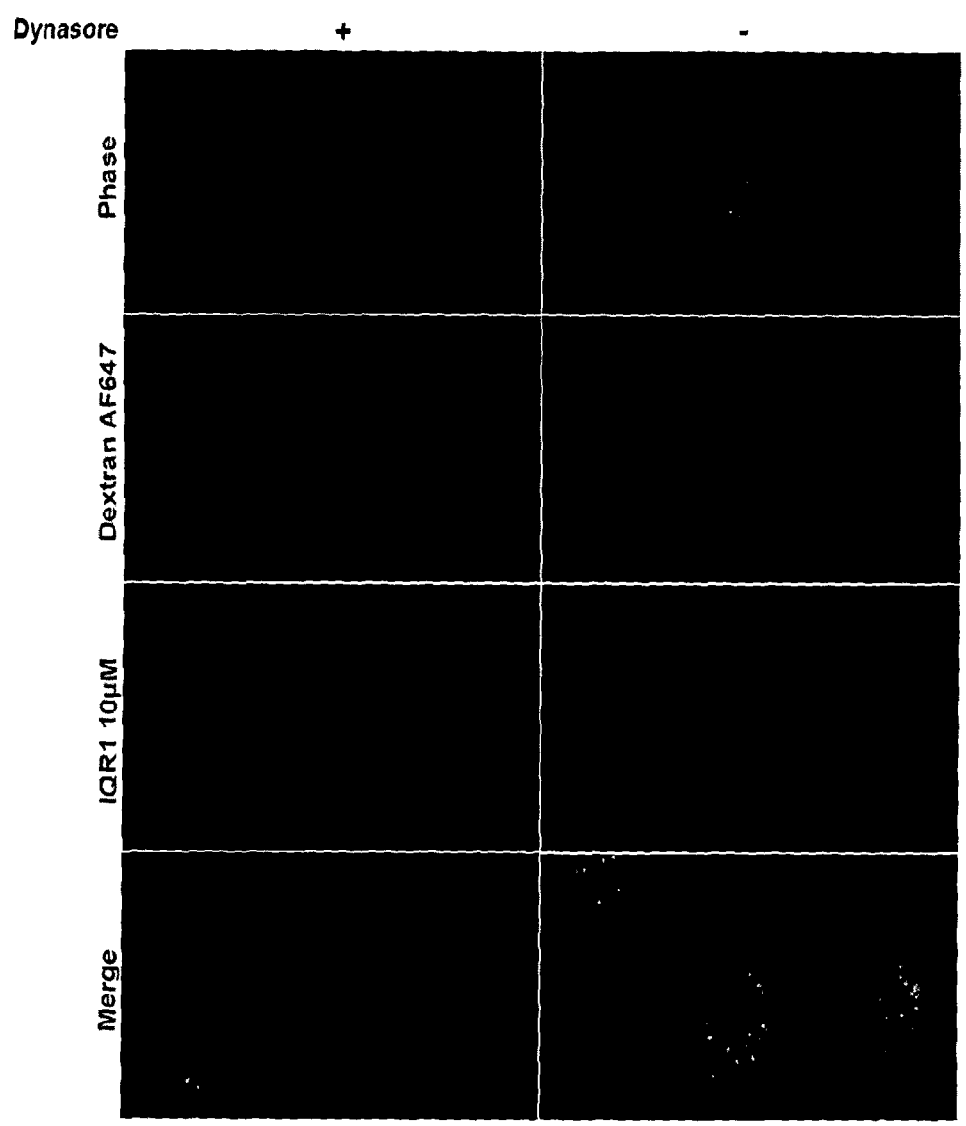
Figure 4:
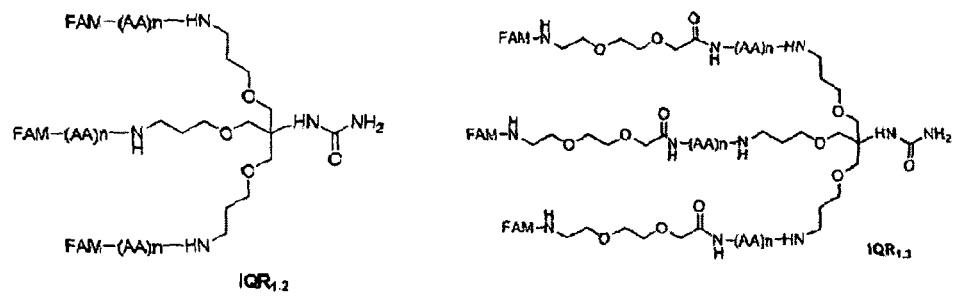
Figure 4:
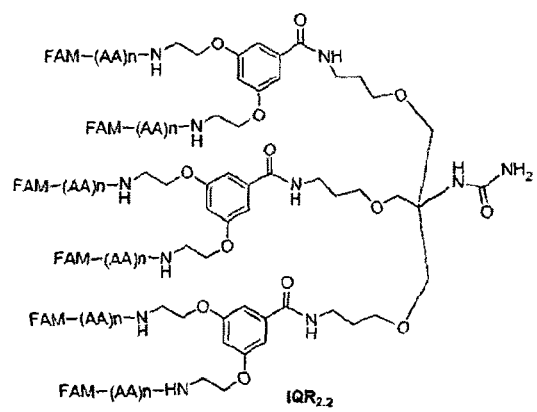
Figure 4:
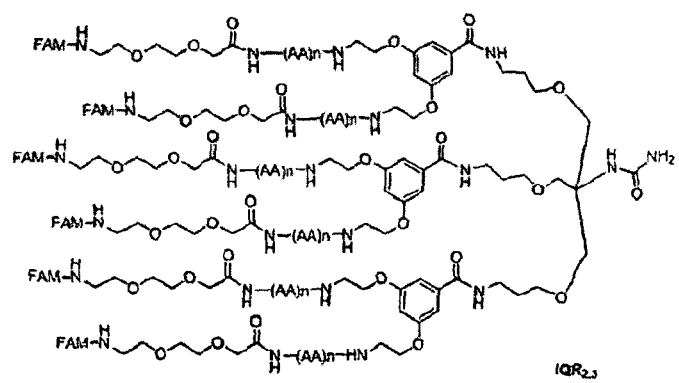
Figure 5:
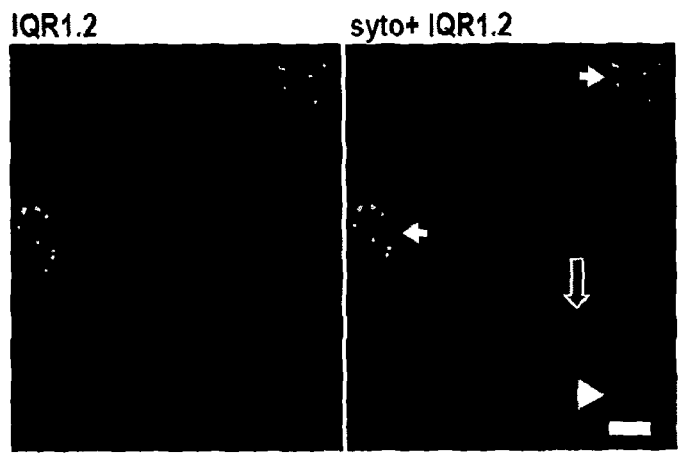
Figure 6:
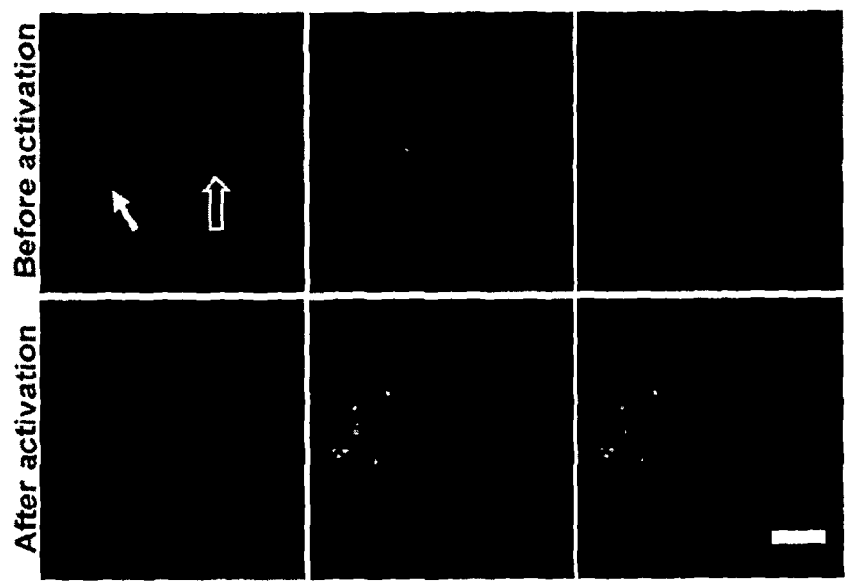
Figure 7:
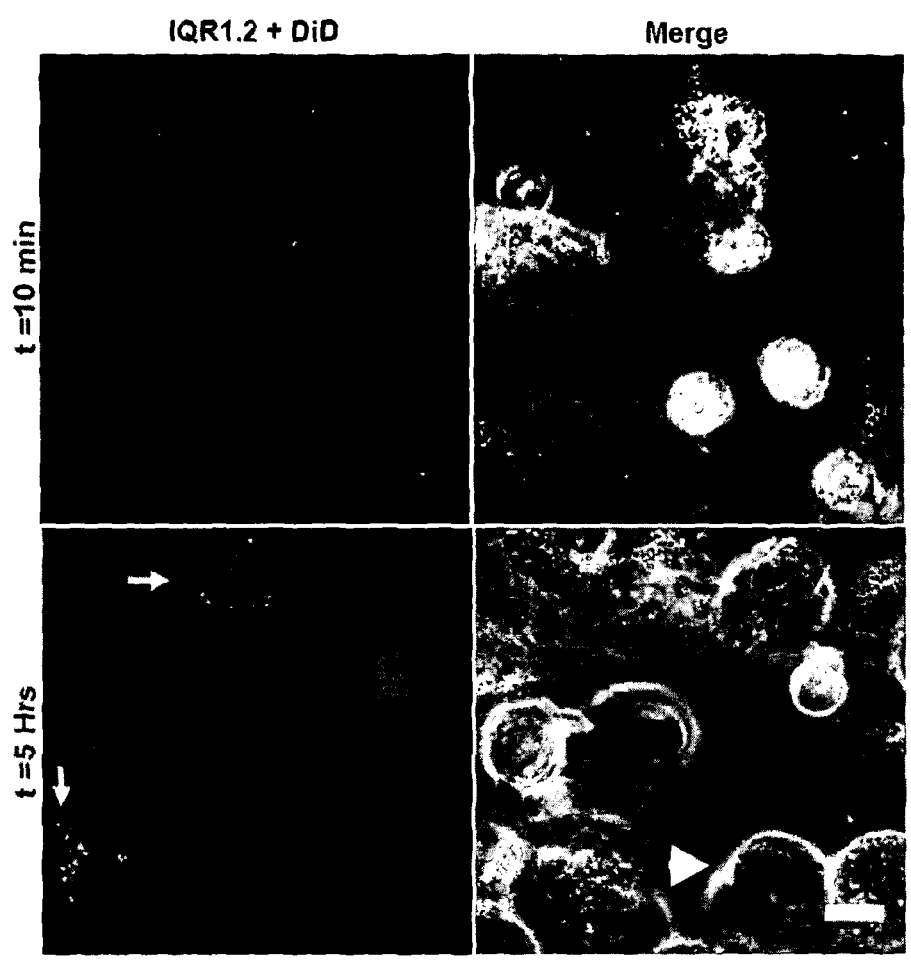
Figure 8:
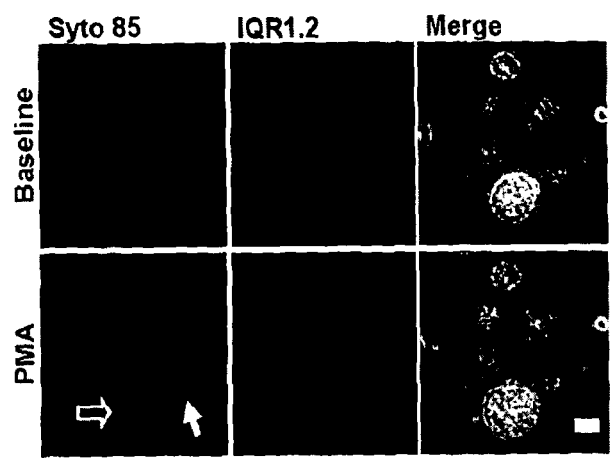
Figure 9:
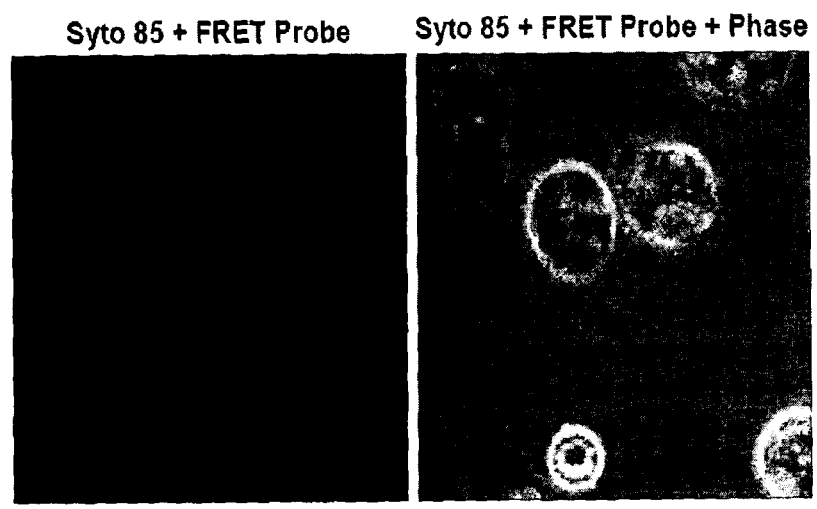
Figure 10:
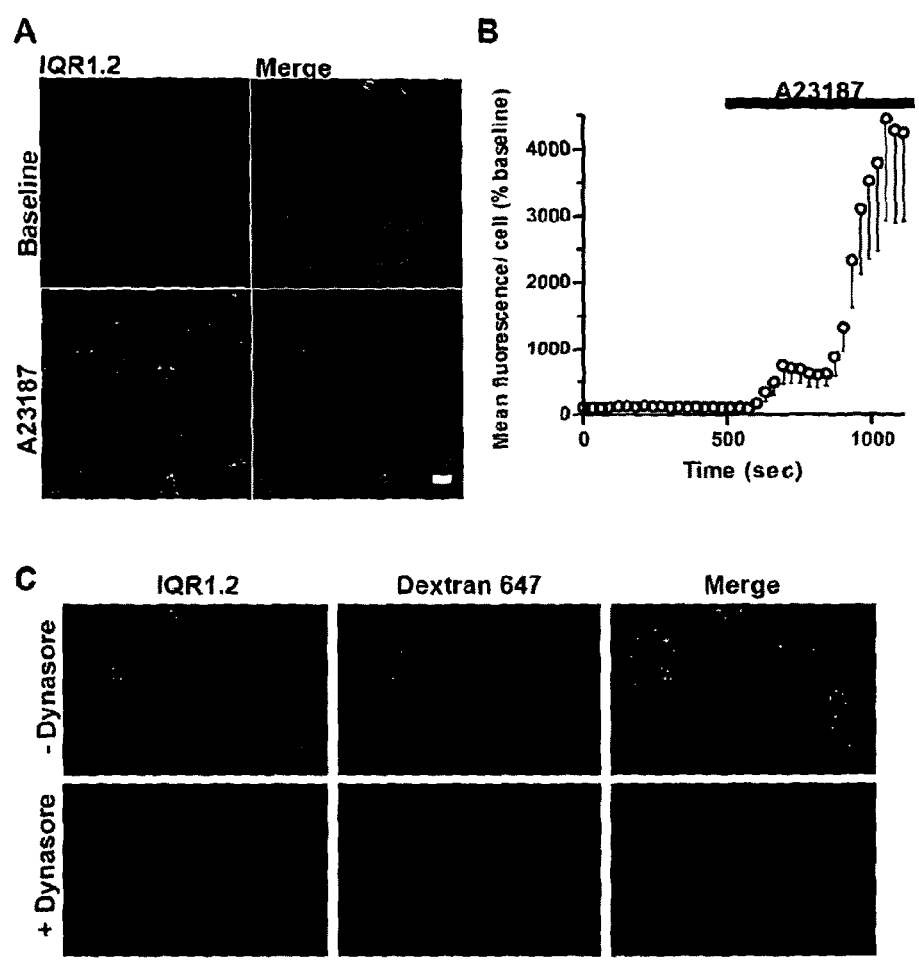

FIG. 3 shows activation of freshly isolated neutrophils with 10 μM A23187 (calcium ionophore) leads to rapid appearance of punctate cell-associated fluorescence which colocalises with dextran647, and is inhibited by treatment with dynasore, suggesting fluid phase IQR1 uptake;

FIG. 4 shows the structures of preferred molecules in accordance with the present invention. (AA)n may be L or D;

FIG. 5 shows human cell specificity: activated PMNs (white arrow), monocytes (open arrow) and lymphocytes (arrow head). Only PMN's activate IQR1.2. Cells are delineated by Syto-85 nuclear dye (red); scale bar: 10 µm;

FIG. 6 shows cell specificity in Bronchoalveolar Lavage (BAL) isolated from patients with inflammatory lung disease: PMNs (white arrow), alveolar macrophage (open arrow). Only activated PMN's activate IQR1.2 Cells are delineated by Syto-85 nuclear dye (red); scale bar: 10 µm;

FIG. 7 shows cell specificity on epithelial cells: Activated PMNs (stained with DiD) were placed upon human alveolar epithelial cells (resolved on phase images) and imaged continuously over 24 h. Epithelial cells did not show uptake over 24 h detected by the IQR1.2. scale bar: 10 µm;

FIG. 8 shows cells retrieved from BAL of mice that had received E. coli lipopolysaccharide 1 day previously. Mixed cellular infiltrate of neutrophils (white arrow full arrows) and macrophages (white arrow open arrows) were obtained. Live confocal imaging of cells at baseline and at 15 min after activation with 10 ng/ml PMA in presence of IQR1.2 probe. No activation observed. Images representative of data obtained from n=3 animals per group carried out on 2 occasions. Scale bar: 10 µm;

FIG. 9 shows activation of freshly isolated human neutrophils with 10 µM A23187 (calcium ionophore) in the presence of a non-dendrimer based FRET probe that doesn't lead to appearance of punctate cell-associated fluorescence;

FIG. 10 shows live time-lapse confocal imaging of probes in primary human neutrophils:

A) Activation of freshly isolated human neutrophils with 10 µM A23187 (calcium ionophore) leads to rapid appearance of punctate cell-associated fluorescence (imaged at 15 min post stimulation) of IQR1.2. Scale bar: 10 µm.

B) Quantification of mean fluorescence intensity per neutrophil over time as percent of baseline prior to activation. Data represents 5 experiments from 3 donors on high power fields with an average of 20 neutrophils per field of view. Data are means and standard errors of mean.

Figure 11:
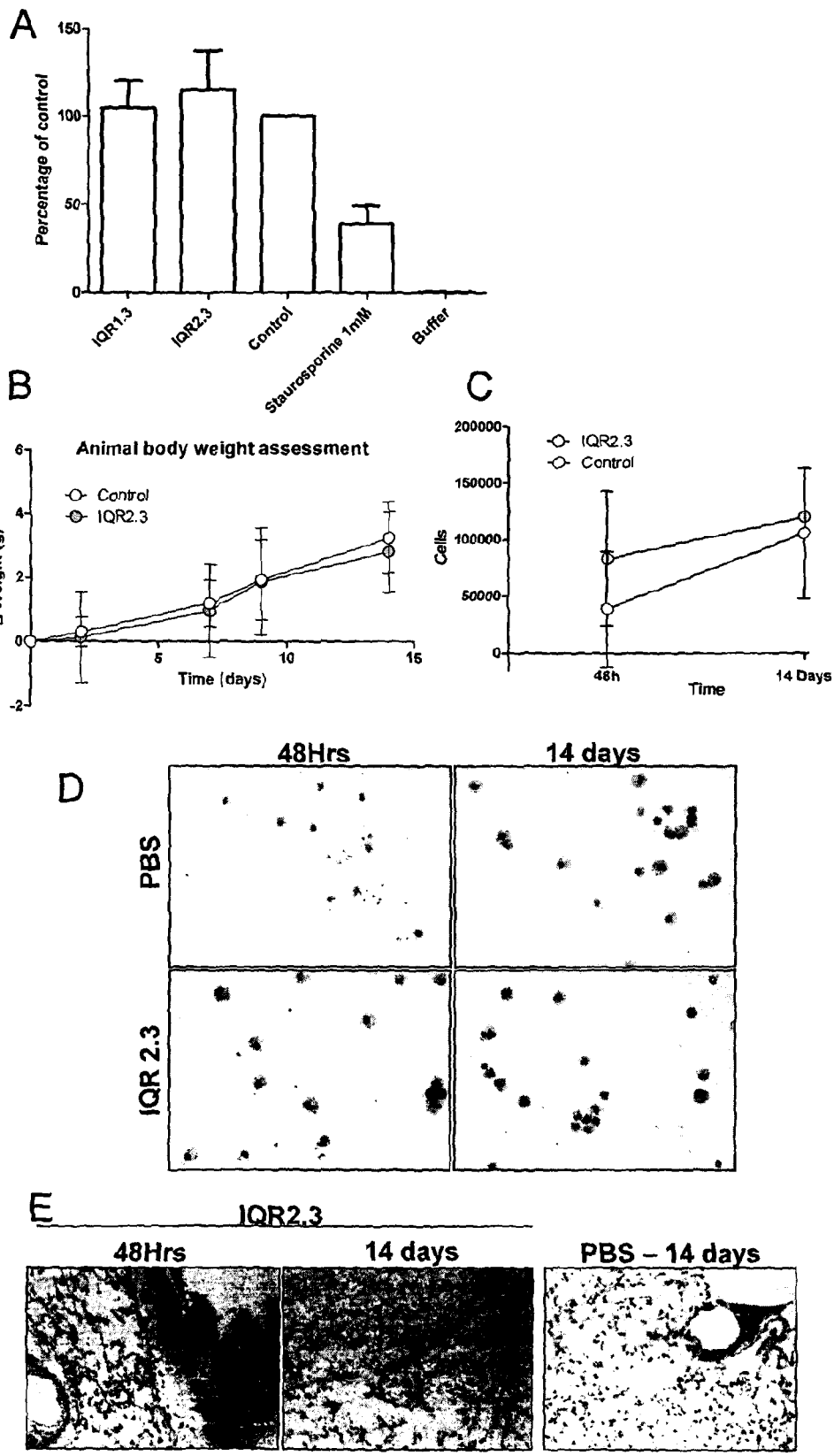

C) This uptake of IQR1.2 as well as dextran 647 is prevented by a pre-treatment with dynamin inhibitor Dynasore;

FIG. 11 shows lack of in vitro and in vivo toxicity of the probe. A) HeLa cells were treated with 100 µM of probe IQR1.3 and IQR2.3 or 1 mM Staurosporine for 24 h. Cell viability was then assessed using Promega cell Titer Glo bioluminescent kit, measuring ATP production in cells. Probes showed no toxicity compared to control;

B) High doses of IQR2.3, 50 µl of 200 µM, was injected intratracheally into 25 g mice. Animals were sacrificed after 48 h and 14 days. Mouse body weight was monitored twice a week. No weight loss was observed after probe injection, compared to control mice. BAL was taken from mice after sacrifice, and cell count (C) as well as cytospins of BAL were performed (D). No difference in total cell number was noticed in BAL, and no neutrophil infiltration was evident at 48 h or 14 days after instillation of IQR2.3. (E) Histological analysis of lungs with H&E staining showed no pulmonary toxicity.

Figure 12:
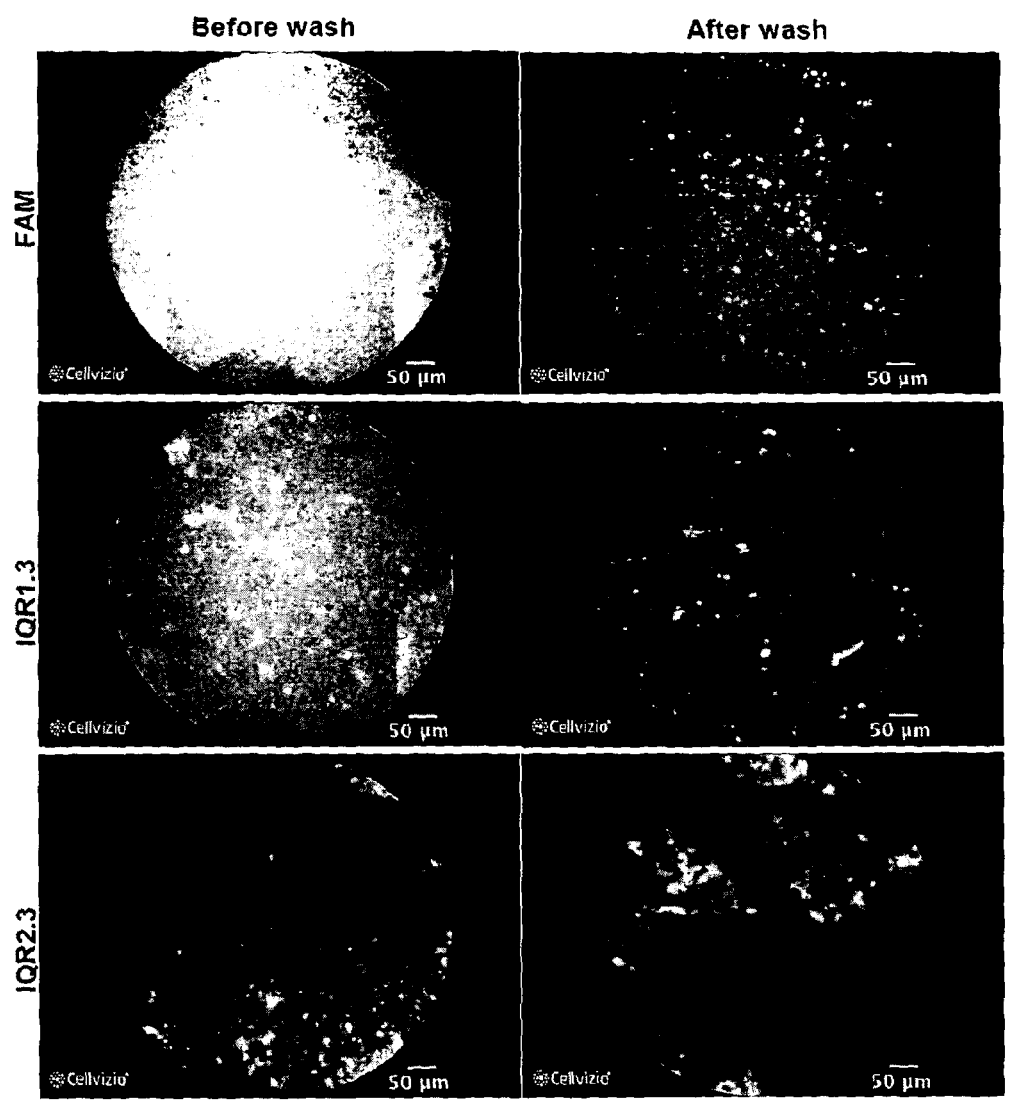
Figure 13:
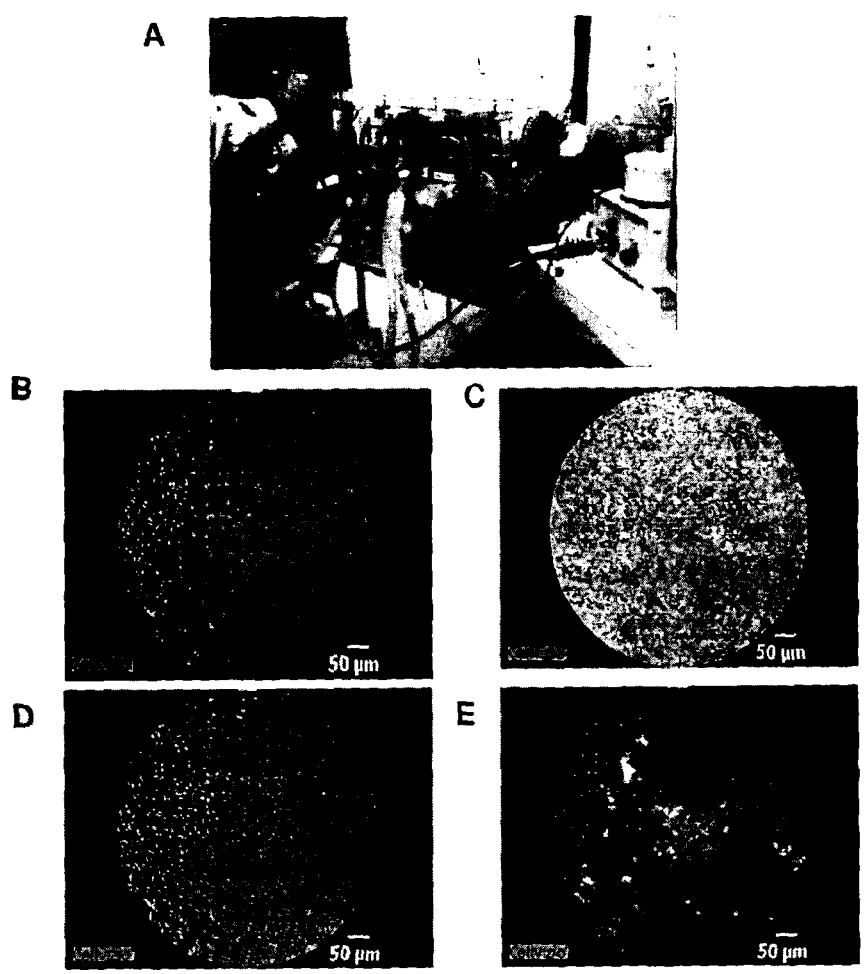

FIG. 12 shows freshly isolated human neutrophils which were activated in an 1.5 ml microtube and then exposed to different IQRs for 15 min and imaged using the Cellvizio® 488 nm fibreoptic confocal system. Then cells were spun down, and probe removed from the medium. Before wash, there is an obvious background difference between FAM, IQR1.3 and IQR2.3. It is not possible to resolve activated cells with FAM alone. After washing, activated cells are visible in all three tubes but with increased signal to noise as quenching increases;

FIG. 13 shows a ventilated sheep model.

(A) shows proof of concept to identify activated cells deep in the ovine lung. (B) Freshly isolated human neutrophils (C), probe alone (IQR 2.3), activated monocytes (D), and activated human neutrophils (E) were instilled into subsegments of the ovine lung. 5 min later 2 mls of IQR 2.3 (final concentration of 5 µg) was instilled into subsegments. Following this Cellvizio® fibreoptic confocal was performed and images acquired. Only segments with activated neutrophils (E) showed optically detectable cells.

Figure 14:
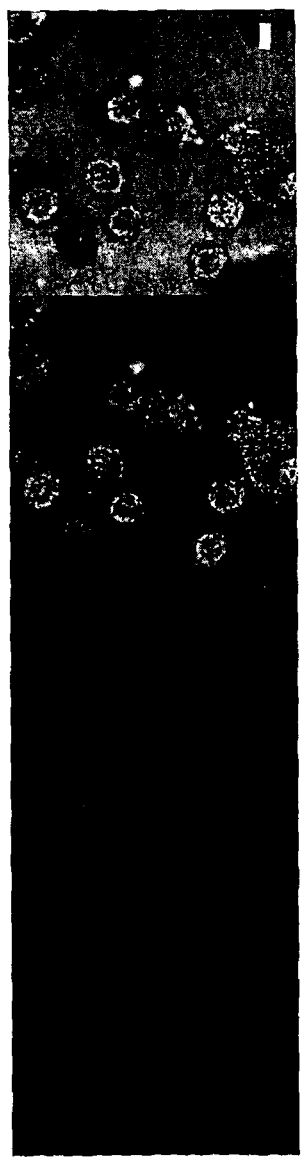

FIG. 14 shows that endocytosis alone is not sufficient for the agents cell-derived signal. Activation of human blood monocytes derived macrophages (cultured 7 days with 10% autologous serum) with the calcium ionophore A23187 (10 µM) in the presence of IQR1 does not lead to the appearance of a punctate cell-associated fluorescence signal as seen in human neutrophils when imaged by laser-scanning confocal microscopy (shown at t+5 minutes). However, punctate uptake of Alexa-647 labelled Dextran, marking fluid-phase endocytosis, is still observed (white arrow). Scale bar: 10 µm.

FIG. 15 shows:

A) IQR 1.2 detects human neutrophils recruited from the circulation by bacterial lipopolysaccharide (LPS; 100 µg) in a ventilated ex vivo sheep lung perfused with whole human blood (see Lee et al. PNAS. 2009) imaged by probe-based Confocal Laser endomicroscopy (pCLE: Cellvizio, alveoflex; 488 nm excitation); and B) No signal is detected when IQR 1.2 is delivered into a control segment of the same lung that has not previously been instilled with LPS

FIG. 16 shows

A) The timecourse of IQR4 de-quenching resulting from incubation with recombinant human neutrophil elastase (HNE; 11.2 ug/ml) was measured using a fluorescent plate-reader. Incubation with HNE leads to a rapid increase in fluorescence from probe IQR4 that is inhibited by the presence of the HNE inhibitor, sivelestat (50 uM);

B) Incubation with human neutrophil lysate (1×10−7/ml) leads to a rapid increase in probe IQR 4 fluorescence that is inhibited by the presence of sivelestat (50 uM).

FIG. 17 shows

A) Activation of freshly isolated human neutrophils with the calcium ionophore A23187 (10 µM) leads to the rapid appearance of a punctate cell-associated fluorescence signal from probe IQR4 when imaged by laser-scanning confocal microscopy (shown at t+15 minutes). Scale bar: 10 µm.

B) Pre-treatment (10 mins) with sivelestat (50 µM) inhibits the appearance of this punctate cell-associated fluorescence from probe IQR4 when neutrophils are activated with A23187 (shown at t+15 minutes). Scale bar: 10 µm.

MATERIALS & METHODS

General Information

Commercially available reagents were used without further purification. NMR spectra were recorded using Bruker AC spectrometers operating at 250, 360 and 500 MHz for $^1$H. Chemical shifts are reported on the δ scale in ppm and are referenced to residual non-deuterated solvent resonances. Normal phase purifications by column chromatography were carried out on silica gel 60 (230-400 mesh).

Analytical reverse-phase high-performance liquid chromatography (RP-HPLC) was performed on an HP1100 system equipped with a Discovery C18 reverse-phase column (5 cm×4.6 mm, 5 μm) with a flow rate of 1 ml/min and eluting with $H_2O$/MeOH/HCOOH (95/5/0.05) to $H_2O$/MeOH/HCOOH (5/95/0.05), over 6 min, holding at 95% MeOH for 4 min, with detection at 254 and 495 nm and by evaporative light scattering.

Semi-preparative RP-HPLC was performed on an HP1100 system equipped with a Phenomenex Prodigy C18 reverse-phase column (250×10 mm, 5 μm) with a flow rate of 2.5 ml/min and eluting with 0.1% HCOOH in $H_2O$ (A) and 0.1% HCOOH in $CH_3CN$ (B), with a gradient of 5 to 95% B over 18 min and an initial isocratic period of 5 min. Electrospray ionization mass spectrometry (ESI-MS) analyses were carried out on an Agilent Technologies LC/MSD Series 1100 quadrupole mass spectrometer (QMS) in an ESI mode. MALDI spectra were acquired on a Voyager-DE™ STR MALDI-TOF MS (Applied Biosystems) with a matrix solution of sinapinic acid (10 mg/ml) in 50% MeCN in water with 0.1% TFA.

Synthesis of Monomer (6)

The monomer 6 was synthesised in six steps[19] as shown in Scheme 1. Thus, the 1,4 addition of the hydroxy groups of 1,1,1-tris(hydroxymethyl)amino-methane onto acrylonitrile, followed by amino protection (Boc), and reduction of the nitrile groups with borane-THF complex gave 3. This was treated with Dde-OH to give the tris-Dde (2-acetyl-dimedone) protected amine 4. Following removal of the Boc protecting group, the isocyanate 6 was prepared following the procedure of Knölker[20].

Scheme 1: Synthesis of monomer (6)

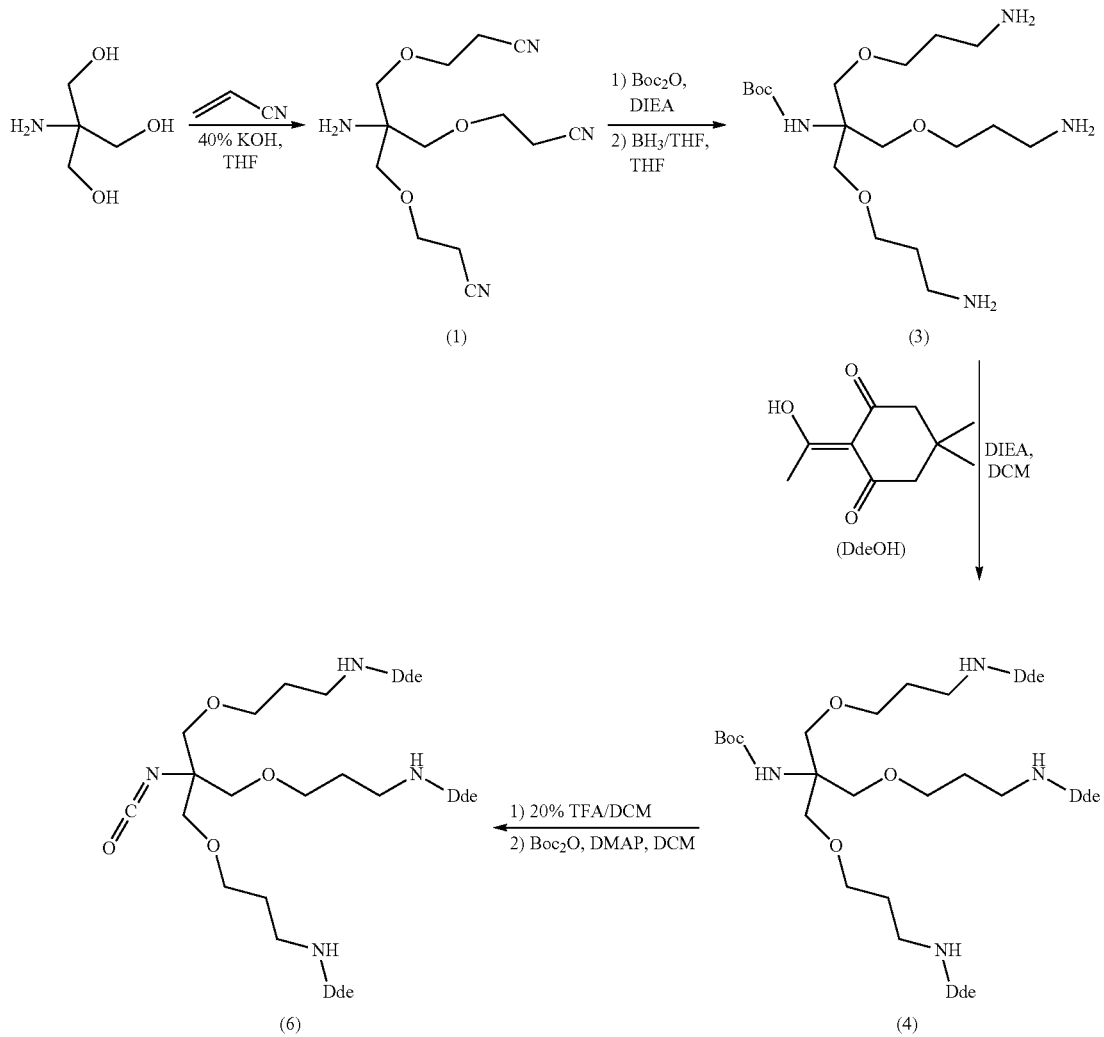

3-[2-Amino-3-(2-cyano-ethoxy)-2-(2-cyano-ethoxymethyl)-propoxy]propionitrile (1)

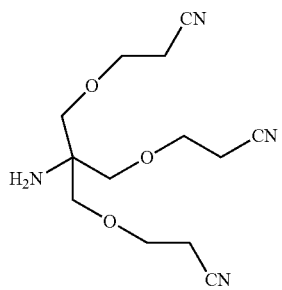 [SMILES: N#CCCOCC(N)(COCCC#N)COCCC#N]

To a solution of tris(hydroxymethyl)aminomethane (6.0 g, 49 mmol) in THF (100 ml), were added sequentially 40% KOH aqueous solution (2 ml) and acrylonitrile (12.9 ml, 200 mmol) and the resulting solution was stirred overnight. The solvent was removed in vacuo and water (100 ml) was added to the residue. The aqueous layer was extracted with dichloromethane (3×100 ml), and the organic layer was dried with $Na_2SO_4$. The organic solvent was evaporated in vacuo and the product (10.7 g of an oil, 73%) was used in the next step without further purification; $^1$H-NMR (500 MHz, $CDCl_3$) δ: 5.3 (s, 2H, $NH_2$), 3.7 (t, J=6 Hz, 6H, $OCH_2$), 3.4 (s, 6H, $CH_2O$), 2.6 (t, J=6 Hz, 6H, $CH_2CN$); MS (ES) m/z: 281 [(M+1)$^+$, 100], 303 [(M+Na)$^+$, 20]. These data are in good agreement with the literature[19].

[2-(2-cyano-ethoxy)-1,1-bis-(2-cyano-ethoxymethyl)-ethyl]-carbamic acid tert-butyl ester (2)

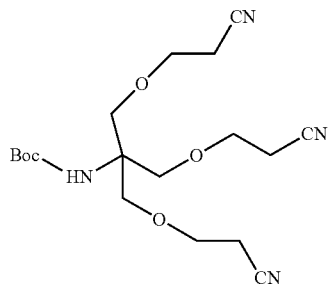 [SMILES: CC(C)(C)OC(=O)NC(COCCC#N)(COCCC#N)COCCC#N]

To a stirred solution of amine (1) (10.7 g, 38 mmol) in THF (100 ml) was added a solution of di-tert-butyl dicarbonate (12.4 g, 57 mmol) in THF (30 ml) at 0° C. followed by the addition of DIEA (10.0 ml, 57 mmol). The reaction was allowed to warm to room temperature and was stirred overnight. The THF was evaporated in vacuo and the residue was dissolved in ethyl acetate (250 ml). The organic layer was washed with 1N $KHSO_4$ (100 ml), saturated $NaHCO_3$ (100 ml) and brine (100 ml), dried over $Na_2SO_4$ and the solvent was evaporated to give the compound (2) as oil (14.4 g, 100%); $^1$H-NMR (500 MHz, $CDCl_3$) δ: 4.9 (s, 1H, NH), 3.8 (t, J=6 Hz, 6H, $OCH_2$), 3.7 (s, 6H, $CH_2O$), 2.6 (t, J=6 Hz, 6H, $CH_2CN$), 1.4 (s, 9H, $CH_3$); MS (ES) m/z: 403 [(M+Na)$^+$, 30], 281 [(M-Boc)$^+$, 100]. Data in good agreement with the literature[19].

[2-(3-Amino-propoxy)-1,1-bis-(3-amino-propoxymethyl)-ethyl]-carbamic acid tert-butyl ester (3)

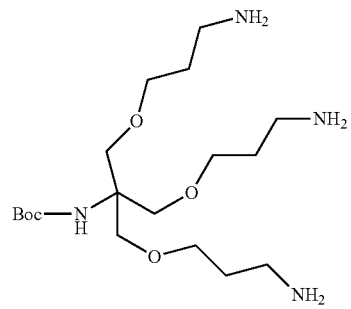 [SMILES: CC(C)(C)OC(=O)NC(COCCCN)(COCCCN)COCCCN]

To a stirred solution of tris-nitrile (2) (4.5 g, 12 mmol) in dry THF (50 ml) was added dropwise $BH_3$.THF complex (1M solution in THF, 72 mmol, 72 ml) and the resulting mixture was stirred at 55° C. for 5 h. Following cooling, 2 M HCl was added to give an apparent pH between 1-2. The mixture was neutralized with NaOH (aq 1 M), and the solvent was removed in vacuo. The crude product was used without purification for the next step.

[2-{3-[1-(4,4-Dimethyl-2,6-dioxocyclohexylidene)ethylamino]propoxy}-1,1-bis-{3-[1-(4,4-dimethyl-2,6-dioxocyclohexylidene)ethylamino]propoxymethyl}-ethyl]-carbamic acid tert-butyl ester (4)

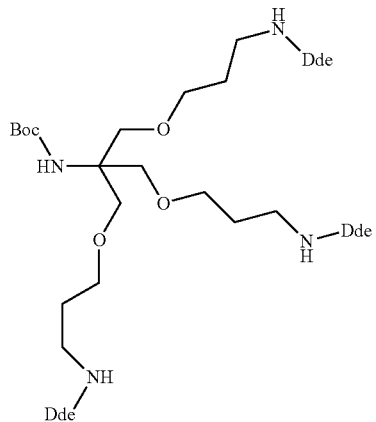

The crude product (3) (4.5 g, 11.4 mmol) was dissolved in methanol (75 ml) and DIPEA (2.4 ml, 13.68 mmol) was added. A solution of 2-acetyl-dimedone[21] (DdeOH, 7.3 g, 40.2 mmol) in dichloromethane (40 ml) was added and the resulting mixture was stirred overnight. The solvents were removed in vacuo and the residue was purified using column chromatography (eluting with dichloromethane/methanol 9/1) to afford the product as a colourless oil (2.4 g, 23%);

$^1$H-NMR (250 Hz, CDCl$_3$) δ: 3.8 (s, 6H, CH$_2$O), 3.7-3.6 (m, 12H, CH$_2$), 2.7 (s, 9H, CH$_3$), 2.5 (s, 12H, CH$_2$), 2.1-2.0 (m, 6H, CH$_2$), 1.5 (s, 9H, CH$_3$), 1.1 (s, 18H, CH$_3$); MS (ES) m/z: 885 [M$^+$, 100]. Data were in good agreement with the literature[19].

[2-{3-[1-(4,4-Dimethyl-2,6-dioxocyclohexylidene)ethylamino]propoxy}-1,1-bis-{3-[1-(4,4-dimethyl-2,6-dioxocyclohexylidene)ethylamino]propoxymethyl}-ethyl]amine (5)

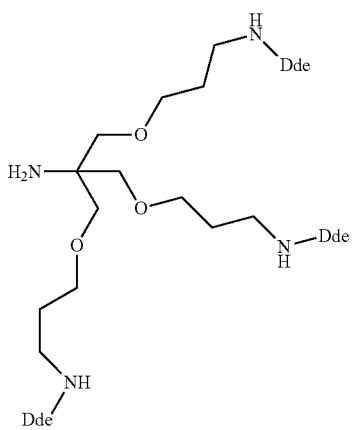

The protected amine (4) (2.3 g, 2.7 mmol) was dissolved in 20% TFA in dichloromethane (40 ml) and the resulting mixture was stirred for 2 h. The solvent was removed in vacuo and the residue was dissolved in dichloromethane (150 ml) and washed with saturated aqueous NaHCO$_3$ solution (75 ml) and water (75 ml). The organic layer was dried with Na$_2$SO$_4$ and the solvents removed in vacuo. The crude product (2.1 g) was used directly in the next step without purification; $^1$H-NMR (360 MHz, CDCl$_3$) δ: 13.1 (bs, 2H, NH$_2$), 3.6 (s, 6H, CH$_2$O), 3.6-3.5 (m, 12H, CH$_2$), 2.5 (s, 9H, CH$_3$), 2.3 (s, 12H, CH$_2$), 1.9-1.8 (m, 6H, CH$_2$), 0.9 (s, 18H, CH$_3$); MS (ES) m/z: 785 [M$^+$, 100], 786 [(M+1)$^+$, 45], 787 [(M+2)$^+$, 10]; HPLC $t_R$=3.75 min. Data were in good agreement with the literature[19].

[2-{3-[1-(4,4-Dimethyl-2,6-dioxocyclohexylidene)ethylamino]propoxy}-1,1-bis-{3-[1-(4,4-dimethyl-2,6-dioxocyclohexylidene)ethylamino]propoxymethyl}-ethyl]isocyanate (6)

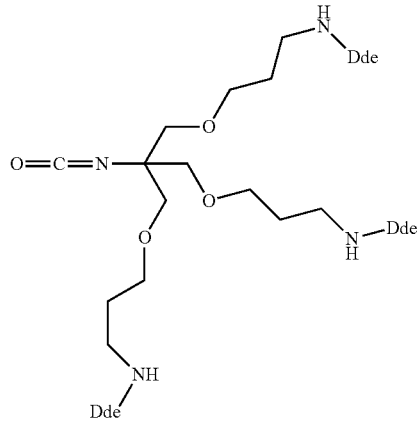

A solution of Boc$_2$O (0.82 g, 3.4 mmol) in dry DCM (10 ml) was added dropwise to a mixture of amine 5 (2.1 g, 2.7 mmol) and DMAP (0.36 g, 2.97 mmol) in dry DCM (20 ml) and the reaction mixture was stirred for 1 h. The solvent was removed in vacuo to give 6 (2.0 g, 91%). The isocyanate 6 was used immediately. $^1$H-NMR (360 MHz, CDCl$_3$) δ: 3.6-3.4 (m, 18H, CH$_2$), 2.5 (s, 9H, CH$_3$), 2.3 (s, 12H, CH$_2$), 1.9-1.8 (m, 6H, CH$_2$), 0.9 (s, 18H, CH$_3$); MS (ES) m/z: 811 [M$^+$, 100]; IR (neat) v (cm$^{-1}$): 2953, 2867, 2244, 1637, 1569, 1461, 1332, 1107, 806, 720. Data were in good agreement with the literature[1].

Synthesis of Monomer (12)

Monomer (12) used in the preparation of 6-branched dendrimer was synthesised in 5 steps using α-resorcylic acid as a starting material (Scheme 2). Esterification of (7) in methanol provides methyl benzoate (8), which then undergoes alkylation with 2-(Boc-amino)ethyl bromide in the presence of potassium carbonate in DMF to yield (9). The latter was then subjected to saponification of the methyl ester by using NaOH/MeOH/dioxane mixture, followed by removal of the Boc protective group using HCl to give amine as the hydrochloride salt (11). Subsequently, the amine salt was selectively protected with FmocOSu to give the branching monomer (12), which was utilised in the Fmoc-based solid support synthesis.

Scheme 2: Synthesis of monomer (12)

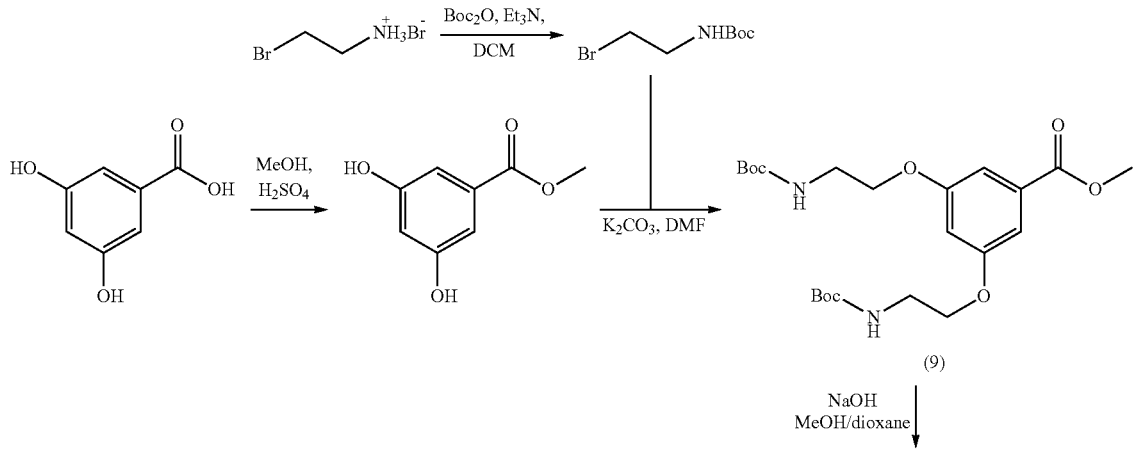

-continued

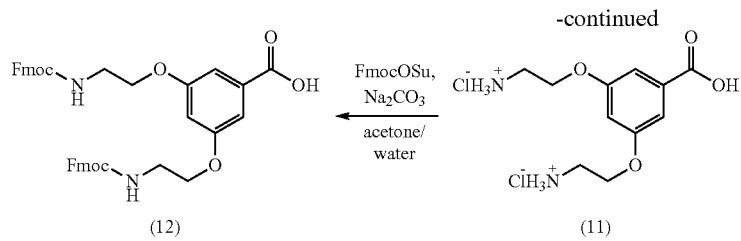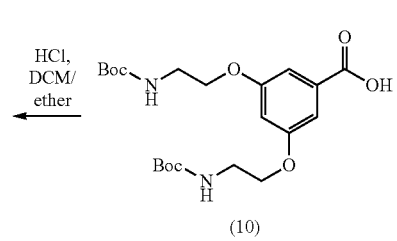

(12)  (11)  (10)

2-N-(-tert-Butoxycarbonylamino)ethyl bromide

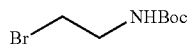

(15)

A suspension of (2-bromoethyl)amine (5.0 g, 25 mmol) and di-tert-butyl dicarbonate (5.4 g, 25 mmol) in dichloromethane (12 ml) was cooled to 0° C., and triethylamine (4 ml, 3.9 mmol) was added dropwise. After stirring for 24 h, dichloromethane (150 ml) was added and the solution was washed with 1 M $KHSO_4$, water and brine, the mixture was dried ($Na_2SO_4$) and concentrated in vacuo. Product was isolated as clear yellow oil (5.22 g, 90%); $^1$H-NMR (500 MHz, $CDCl_3$) δ: 4.96 (1H, br s, NH), 3.61-3.43 (4H, m, $BrCH_2$, $CH_2NH$), 1.48 (9H, s, $C(CH_3)_3$); $^{13}$C-NMR (125 MHz, $CDCl_3$) δ: 155.4 (C=O), 79.6 (C), 42.2 ($CH_2$), 32.4 ($CH_2$), 28.1 ($CH_3$). Data were in good agreement with the literature[22].

Methyl 3,5-dihydroxybenzoate (8)

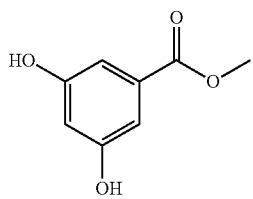

To a solution of 3,5-dihydroxybenzoic acid (5.0 g, 32 mmol) in methanol (170 ml) was added a catalytic amount of sulphuric acid (0.3 ml). After stirring at reflux overnight, the mixture was cooled and neutralized with 4M NaOH (aq. solution). After concentration, the residue was dissolved in ethyl acetate and washed with water and brine. The organic layer was dried ($Na_2SO_4$) and concentrated in vacuo. Compound 2 was isolated as a white solid (5.13 g, 95%); m.p. 164-165° C. (ethyl acetate); $^1$H-NMR (500 MHz, d6-DMSO) δ: 9.65 (2H, s), 6.81 (2H, d, J 2.3 Hz, $CH_{ar}$), 6.43 (1H, d, J 2.3 Hz, $CH_{ar}$), 3.78 (3H, s, $CH_3$); $^{13}$C-NMR (125 MHz, d6-DMSO) δ: 166.2 (C=O), 158.4 (C×2), 131.2 (C), 107.1 (CH), 107.0 (CH×2), 51.9 ($CH_3$); MS (ES)$^-$ m/z: 167 [M−H]$^-$; HPLC $t_R$=3.11; IR (neat) v (cm$^{-1}$): 3229, 1688, 1600, 1486, 1305, 1161, 1102, 995, 765. Data were in good agreement with the literature[22].

Methyl 3,5-[di-N-(-tert-butoxycarbonyl)ethoxy]-benzoate (9)

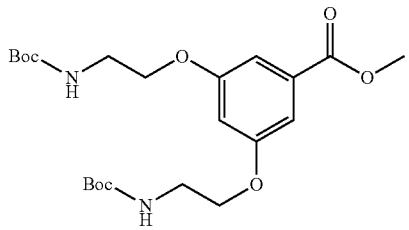 [SMILES: COC(=O)c1cc(OCCNC(=O)OC(C)(C)C)cc(OCCNC(=O)OC(C)(C)C)c1]

A mixture of 2-(boc-amino)ethyl bromide (36 g, 170 mmol), compound (8) (11.4 g, 68 mmol), potassium carbonate (37.3 g, 270 mmol) in anhydrous dimethylformamide (110 ml) was stirred at 50° C. for 16 h. The mixture was filtered through Celite® and the filtrate was reduced. The residue was dissolved in ethyl acetate and washed with water and brine, the organic layer was dried ($Na_2SO_4$) and concentrated in vacuo. Crystallisation (EtOAc/hexane) afforded compound (3) as a white solid (11.9 g). Remaining mother liquor was reduced in vacuo and the residual oil was purified with silica column chromatography using 20% EtOAc in hexane to give 13.7 g of (9) (total yield 25.6 g, 83%); m.p. 96-98° C. (EtOAc/hexane); $^1$H-NMR (500 MHz, $CDCl_3$) δ: 7.18 (2H, d, J 2.2 Hz, $CH_{ar}$), 6.63 (1H, t, J 2.2 Hz, $CH_{ar}$), 4.98 (2H, s, NH), 4.06 (4H, t, J 5.0 Hz, $CH_2$), 3.92 (3H, s, $CH_3$), 3.60-3.56 (4H, m, $CH_2$), 1.47 (18H, s, $C(CH_3)_3$); $^{13}$C-NMR (125 MHz, $CDCl_3$) δ: 166.5 (C=O), 159.6 (C×2), 155.8 (C=O), 132.1 (C), 108.1 (CH×2), 106.4 (CH), 79.5 (C), 67.5 ($CH_2$), 52.1 ($CH_3$), 40.0 ($CH_2$), 28.3 ($CH_3$); MS (ES)$^+$ m/z: 477 [M+Na]$^+$; HPLC $t_R$=4.46 min; IR (neat) v (cm$^{-1}$): 3281, 1722, 1687, 1537, 1276, 1229, 1066, 841, 766. Data were in good agreement with the literature[22].

3,5-[di-N-(tert-butoxycarbonyl)ethoxy]-benzoic acid (10)

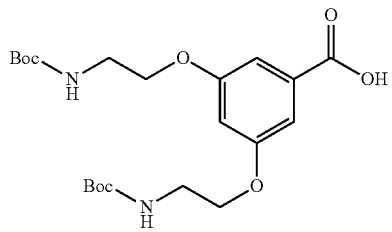 [SMILES: CC(C)(C)OC(=O)NCCOc1cc(OCCNC(=O)OC(C)(C)C)cc(C(=O)O)c1]

Compound 9 (1.06 g, 2.3 mmol) was dissolved in dioxane/methanol/4M NaOH$_{(aq)}$ (14:5:2, 20 ml) and stirred for 5 h. The pH of the mixture was adjusted to 2 with 1 M KHSO$_2$ and the mixture was concentrated in vacuo. The residue was dissolved in dichloromethane and water. The organic layer was washed with water and brine, and dried (Na$_2$SO$_4$). Compound (10) was isolated as a white solid (985 mg, 96%); m.p. 132-134° C. (dichloromethane); $^1$H-NMR (500 MHz, CDCl$_3$) δ: 7.21 (2H, broad s, CH$_{ar}$), 6.71 (1H, broad s, CH$_{ar}$), 4.51 (2H, s, NH), 4.16-4.21 (4H, m, CH$_2$), 3.58-3.52 (4H, m, CH$_2$), 1.52 (18H, s, C(CH$_3$)$_3$); $^{13}$C-NMR (125 MHz, CDCl$_3$) δ: 159.8 (C=O), 159.6 (C×2), 157.3 (C=O), 156.1 (C=O), 131.5 (C), 108.5 (CH×2), 107.6 (CH), 79.9 (C), 67.5 (CH$_2$), 67.4 (CH$_2$), 67.1 (CH$_2$×2), 40.1 (CH$_2$), 28.4 (CH$_3$); MS (ES)$^+$ m/z: 463 [M+Na]$^+$; HRMS (ESI)$^+$ m/z: Calculated for C$_{21}$H$_{32}$N$_2$O$_8$ [M+H]$^+$ 441.2231. Found 441.2283; HPLC t$_R$=4.26 min; IR (neat) ν (cm$^{-1}$): 3389, 2980, 1715, 1598, 1518, 1174, 1070, 871, 786.

3,5-(Di-aminoethoxy)-benzoic acid, hydrochloride (11)

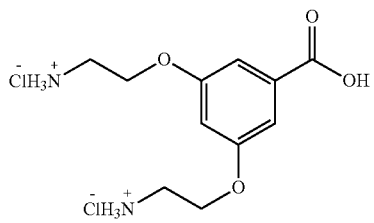

Benzoic acid (10) (2.28 g, 5.2 mmol) was dissolved in dichloromethane (30 ml) and diethyl ether (30 ml) saturated with hydrochloric acid was added. After stirring for 2 h, the mixture was concentrated in vacuo. The hydrochloride salt (11) was obtained as a white solid (1.64 g, quantitative); m.p.<250° C. (dichloromethane/ether); $^1$H-NMR (500 MHz, D$_2$O) δ: 7.20 (2H, d, J 2.2 Hz, CH$_{ar}$), 6.81 (1H, t, J 2.2 Hz, CH$_{ar}$), 4.23 (4H, t, J 5.0 Hz, CH$_2$), 3.38 (4H, t, J 5.0 Hz, CH$_2$); $^{13}$C-NMR (125 MHz, D$_2$O) δ: 170.6 (C=O), 158.7 (C×2), 128.0 (C), 108.6 (CH×2), 106.5 (CH), 64.2 (CH$_2$), 38.8 (CH$_2$); MS (ES)$^+$ m/z: 241 [M+Na]$^+$; HRMS (ES)$^+$ m/z: Calculated for C$_{11}$H$_{16}$N$_2$O$_4$ [M+H]$^+$ 241.118. Found 241.120; HPLC t$_R$=0.77 min.

3,5-[Di(2-fluorenylmethyloxycarbonylamino)ethoxy]-benzoic acid (12)

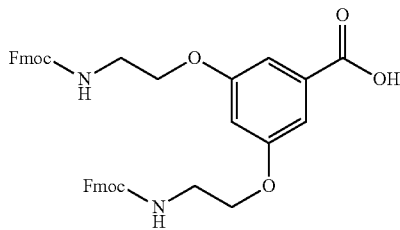

Hydrochloride salt (11) (717 mg, 2.2 mmol) was dissolved in acetone:water (1:1, 100 ml) containing sodium carbonate (950 mg, 9 mmol). To this solution was added Fmoc-Osu (1.57 g, 4.6 mmol) in acetone (25 ml) dropwise at room temperature. The solution was stirred at room temperature for 18 h. The reaction mixture was concentrated and the residue dissolved in water and extracted with ether (2×50 ml). The aqueous layer was cooled in an ice bath and acidified with 2M HCl to pH3. The white solid (12) obtained was filtered, washed with water and dried under vacuum (1.15 g, 77%); m.p. 192-195° C. (water); $^1$H-NMR (500 MHz, d6-DMSO) δ: 13.01 (1H, broad s, OH), 7.87 (4H, d, J 7.5 Hz, CH$_{ar}$), 7.67 (4H, d, J 7.5 Hz, CH$_{ar}$), 7.51 (2H, t, J 5.5 Hz, NH), 7.39 (4H, t, J 7.5 Hz, CH$_{ar}$), 7.29 (4H, t, J 7.5 Hz, CH$_{ar}$), 7.06 (2H, d, J 2.0 Hz, CH$_{ar}$), 6.95 (1H, broad s, CH$_{ar}$), 4.31 (4H, d, J 6.9 Hz, 2×CH$_2$), 4.21 (2H, t, J 6.9 Hz, 2×CH), 4.01 (4H, t, J 5.5 Hz, CH$_2$), 3.38-3.35 (4H, m, CH$_2$); $^{13}$C-NMR (125 MHz, d6-DMSO) δ: 159.8 (C=O), 156.7 (C=O×2), 144.2 (C×4), 141.2 (C×4), 128.0, 128.9, 127.5 & 125.6 (CH), 120.5 (CH×2), 108.2 (CH), 67.0 (CH$_2$×2), 65.8 (CH$_2$×2), 55.1 (CH$_2$×2), 47.2 (CH×2); MS (ES)$^+$ m/z: 707 [M+Na]$^+$; HRMS (ESI)$^+$ m/z: Calculated for C$_{41}$H$_{36}$N$_2$O$_8$ [M+H]$^+$ 685.2544. Found 685.2616; HPLC t$_R$=4.81 min; IR (neat) ν (cm$^{-1}$): 3320, 1699, 1603, 1543, 1449, 1268, 1168, 916, 760.

Synthesis of Resin-Bound Dendrimeric Scaffolds (14) and (15)

Resin-Bound 3-Branched Dendrimeric Scaffold (14)

Resin 13 was synthesized using a 4-[(2,4-dimethoxyphenyl)-(Fmoc-amino)methyl]phenoxyacetic acid (Rink amide linker) attached to aminomethyl PS resin (1.6 mmol/g, 1% DVB, 100-200 mesh). Thus, Fmoc-Rink-amide linker (2.6 g, 4.8 mmol) was dissolved in DMF (16 ml) and HOBt (0.7 g, 4.8 mmol) was added and the mixture was stirred for 10 min. DIC (0.7 ml, 4.8 mmol) was then added and the resulting mixture was stirred for further 5 min. The solution was added to aminomethyl polystyrene resin (1 g, 1.6 mmol/g) and shaken for 2 h. The resulting resin was washed with DMF (3×10 ml), DCM (3×10 ml) and MeOH (3×10 ml).

Fmoc—Deprotection

To the resin (pre-swollen in DCM) was added 20% piperidine in DMF (5 ml) and the reaction mixture was shaken for 10 min. The solution was then drained and the resin was washed with DMF (3×10 ml), DCM (3×10 ml) and MeOH (3×10 ml). This procedure was repeated twice.

Isocyanate Coupling

To resin 13 (625 mg, 1.0 mmol), pre-swollen in DCM (10 ml), was added a solution of isocyanate monomer 6 (2.7 g, 3.0 mmol), DIPEA (0.5 ml, 3.0 mmol) and DMAP (7 mg, 0.6 mmol) in a mixture of DCM/DMF (1:1, 10 ml) and the mixture was shaken overnight and the reaction was monitored by a quantitative ninhydrin test. The solution was drained and the resin was washed with DMF (3×20 ml), DCM (3×20 ml), MeOH (3×20 ml) and finally by ether (3×20 ml).

Scheme 3: Synthesis of 3 and 6-branched dendrimeric scaffolds (14) and (15)
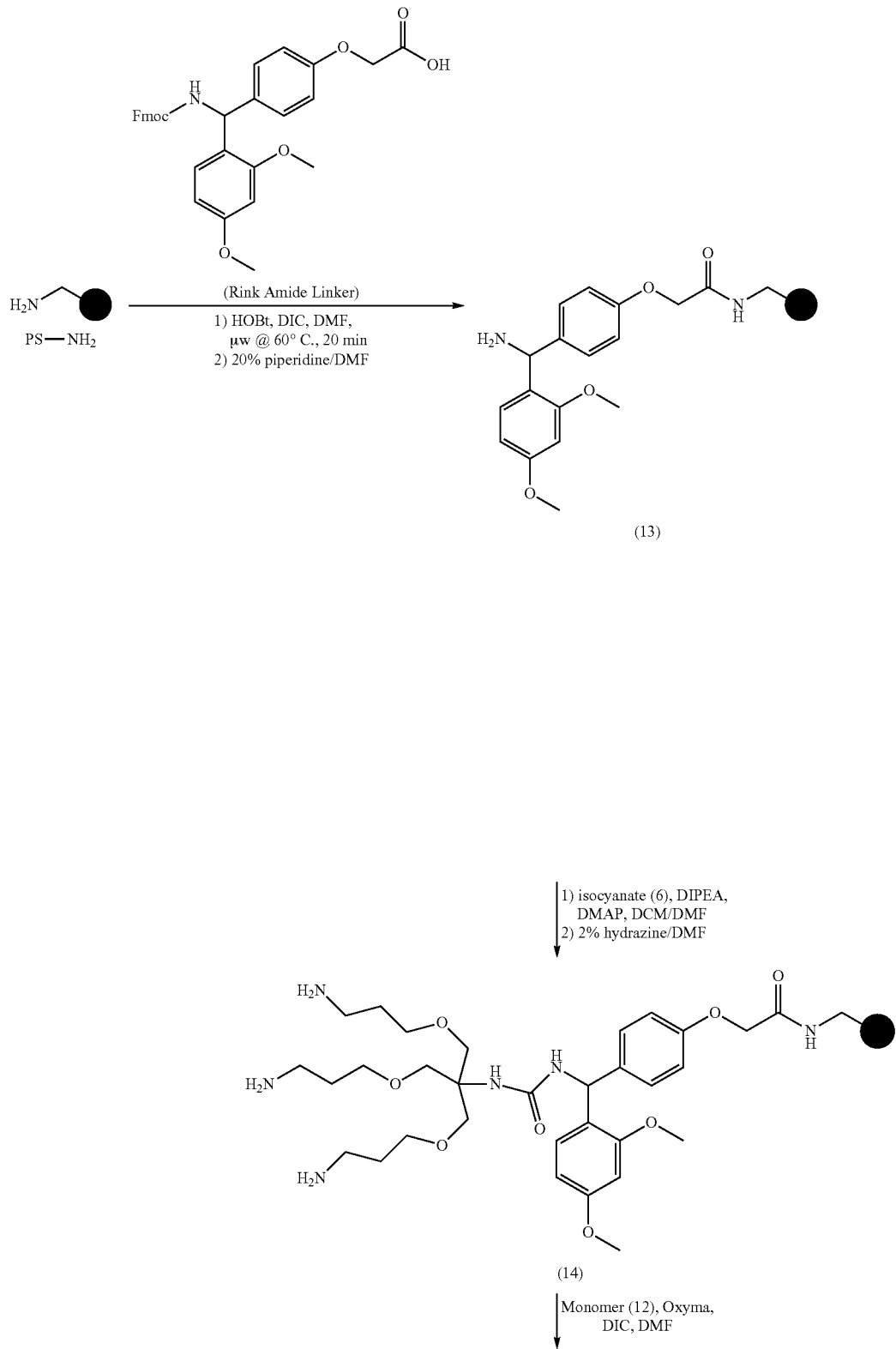

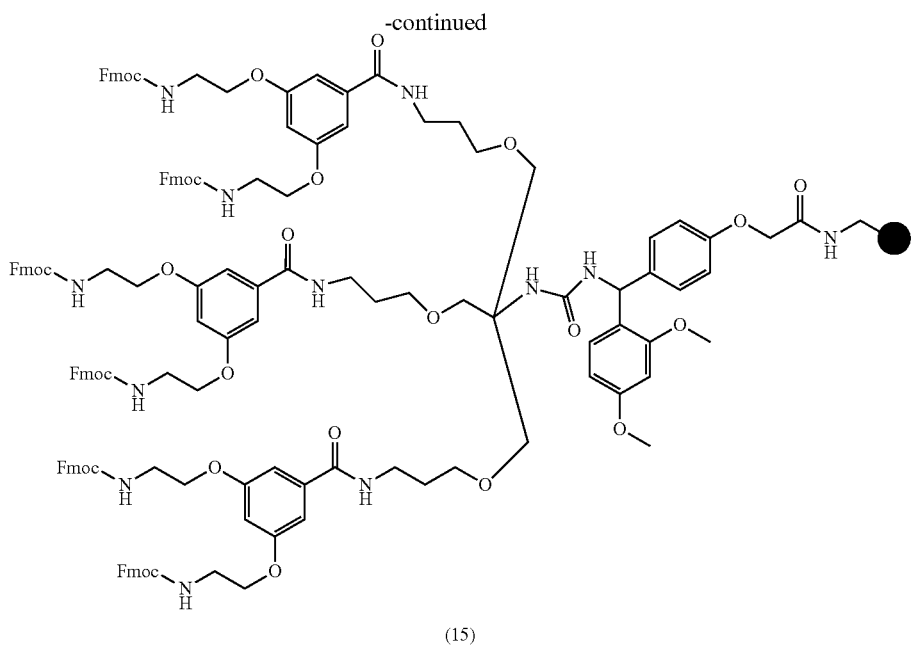

(15)

Dde—Deprotection

To the resin (200 mg, 0.32 mmol), pre-swollen in DCM (5 ml), was added 2% hydrazine in DMF (3 ml) and the reaction mixture was shaken for 2 h. The solution was then drained and the resin (14) was washed with DMF (3×20 ml), DCM (3×20 ml) and MeOH (3×20 ml).

Resin-Bound 6-Branched Dendrimeric Scaffold (15)

A solution of the monomer (12) (379 mg, 0.55 mmol, 4.5 eq) and oxyma (79 mg, 0.55 mmol, 4.5 eq) in DMF (0.5 ml, 1 M) was stirred for 10 min. DIC (87 μL, 0.55 mmol, 4.5 eq) was then added and the resulting solution was stirred for further 2 min. The solution was then added to resin (14) (100 mg, 0.12 mmol, 1 eq), pre-swollen in DCM (2 ml), and the reaction mixture was shaken for 2 h. The solution was drained and the resin (9) was washed with DMF (3×2 ml), DCM (3×2 ml) and MeOH (3×2 ml).

Synthesis of reporters IQR$_1$, IQR$_2$ and IQR$_3$

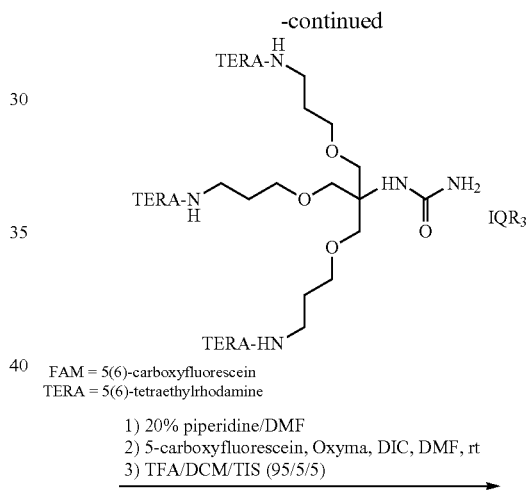

FAM = 5(6)-carboxyfluorescein
TERA = 5(6)-tetraethylrhodamine 1) 20% piperidine/DMF
2) 5-carboxyfluorescein, Oxyma, DIC, DMF, rt
3) TFA/DCM/TIS (95/5/5)

(15)

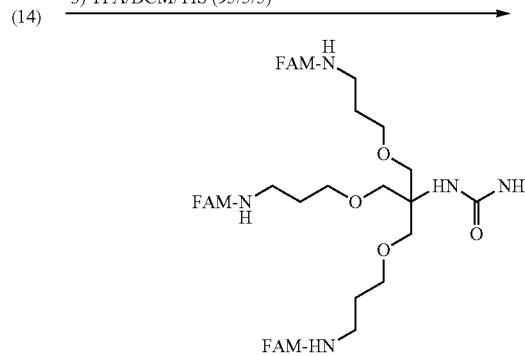

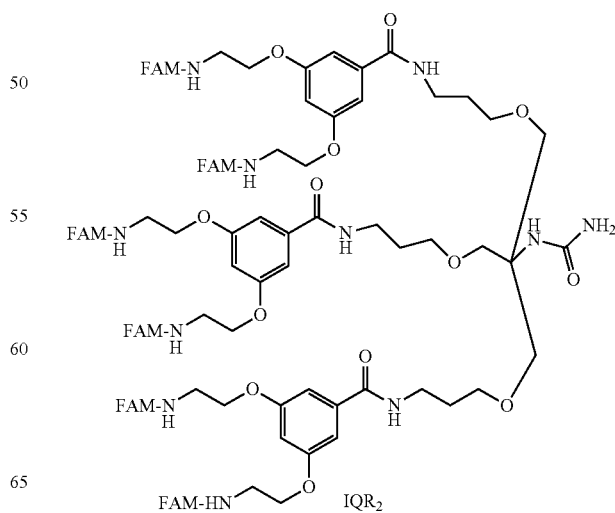

5(6)-carboxyfluorescein labelling

A solution of 5(6)-carboxyfluorescein (10 eq) and oxyma (10 eq) in DMF (700 μl) was stirred for 10 min. DIC (10 eq) was then added and the resulting solution was stirred for further 5 min. This solution was added to the appropriate resin (1 eq), pre-swollen in DCM, and the reaction mixture was shaken for 6 h. The solution was drained and the resin washed with DMF (×3), DCM (×3) and MeOH (×3). The coupling reactions were monitored by a quantitative ninhydrin test[23]. Before cleavage, the resin was washed with 20% piperidine to remove any fluorescein phenol esters[24].

5(6)-tetraethylrhodamine labelling

A solution of 5(6)-tetraethylrhodamine (10 eq) and oxyma (10 eq) in DMF (700 μl) was stirred for 10 min. DIC (10 eq) was then added and the resulting solution was stirred for further 5 min. This solution was added to the appropriate resin (1 eq), pre-swollen in DCM, and the reaction mixture was shaken for 6 h. The solution was drained and the resin washed with DMF (×3), DCM (×3) and MeOH (×3). The coupling reactions were monitored by a quantitative ninhydrin test.

Synthesis of reporters IQR$_{1.2}$, IQR$_{1.3}$, IQR$_{2.2}$ and IQR$_{2.3}$

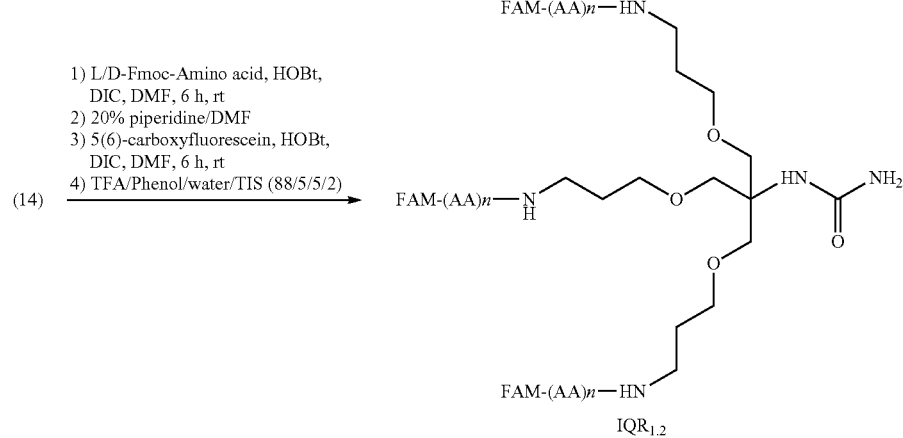

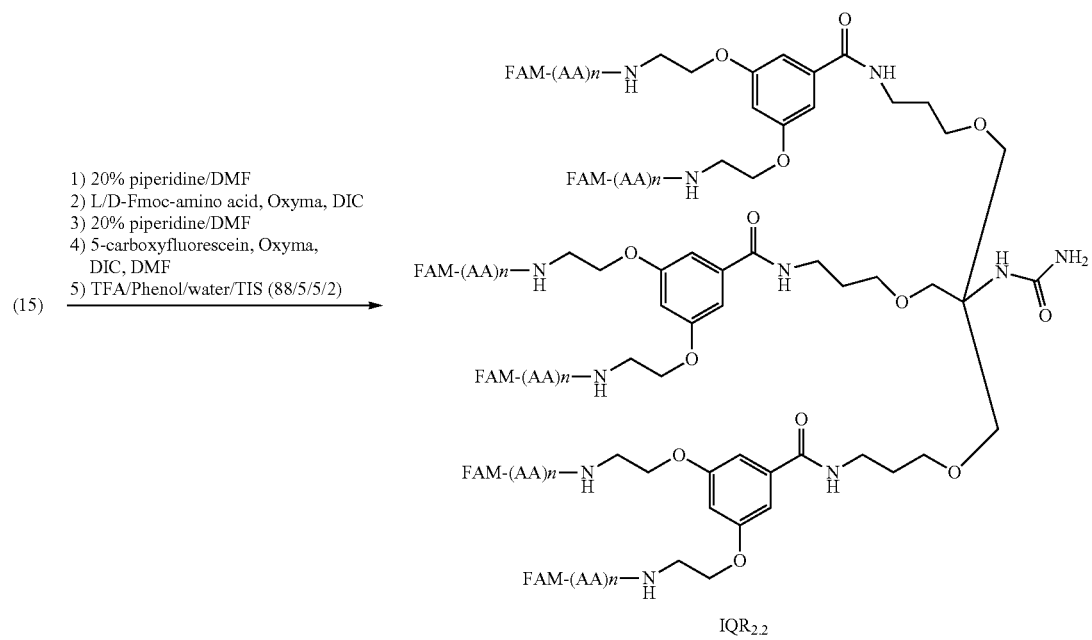

Peptide Coupling

A solution of the appropriate D- or L-Fmoc-amino acid (3 eq per amine) and HOBt or Oxyma (3 eq per amine) in DMF (1 M) was stirred for 10 min. DIC (3 eq per amine) was then added and the resulting solution was stirred for further 5 min. The solution was then added to the appropriate resin 14/15 (1 eq), pre-swollen in DCM (10 ml), and the reaction mixture was shaken for 1-3 h. The solution was drained and the resin was washed with DMF (3×20 ml), DCM (3×20 ml) and MeOH (3×20 ml). The coupling reactions were monitored by a quantitative ninhydrin test[23].

DCM (3×20 ml) and MeOH (3×20 ml). The coupling reactions were monitored by a quantitative ninhydrin test[23].

TFA Cleavage and Purification of Reporters $IQR_1$-$IQR_3$

The appropriate resin (50 mg), pre-swollen in DCM, and treated with a cleavage cocktail of TFA/DCM/TIS (95/5/5, 500 µl) for 2.5 h. The solution was drained and the resin was washed with the cleavage cocktail and the solution was removed in vacuo The crude material was dissolved in a minimum amount of cleavage cocktail (300 µl) and added to ice-cold ether (7.5 ml). The precipitated solid was collected by centrifugation and the solvent removed by decantation

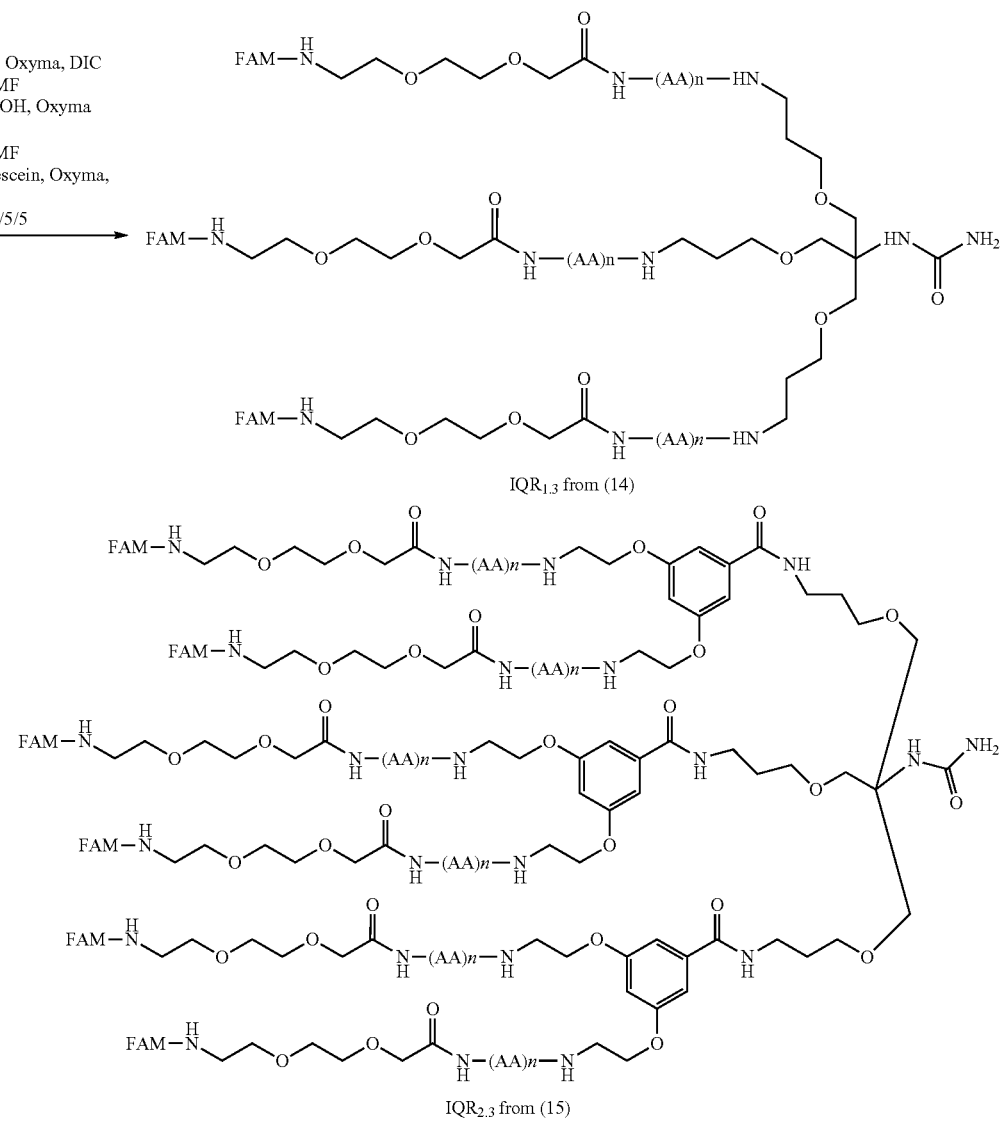

and the precipitate was washed with cold ether (3×5 ml). The precipitate was then purified by reverse phase preparative HPLC and the required fractions were pooled and lyophilized to afford $IQR_1$-$IQR_3$; Reporter $IQR_1$: HPLC: $t_R$=4.3 min, purity>98% by ELSD; MALDI: $C_{77}H_{63}N_5O_{22}$: [M+] calcd: 1410.34, [M+2]+ found: 1412.38; Reporter $IQR_{1,2}$: HPLC $t_R$=8.2 min, purity>98% by ELSD; Reporter $IQR_{1,3}$: HPLC $t_R$=2.67 min purity>98% by ELSD; Reporter $IQR_2$: HPLC $t_R$=3.55 min; HRMS (ESI)+ m/z: Calcd for $C_{173}H_{135}N_{11}O_{49}$ ([M+4H]/4)+788.9692. Found 788.9799;

Pegylation

A solution of the {2-[2-(Fmoc-amino)ethoxy]ethoxy}acetic acid (3 eq per amine) and Oxyma (3 eq per amine) in DMF (1 M) was stirred for 10 min. DIC (3 eq per amine) was then added and the resulting solution was stirred for further 5 min. The solution was then added to the appropriate resin 14/15 (1 eq), pre-swollen in DCM (10 ml), and the reaction mixture was shaken for 1 h. The solution was drained and the resin was washed with DMF (3×20 ml), IR (neat) v (cm$^{-1}$): 1590.1, 1454.4, 1175.2, 1113.6, 852.6, 720.5; Reporter IQR$_{2.2}$: HPLC t$_R$=5.17 min purity>98% by ELSD; Reporter IQR$_{2.3}$: HPLC t$_R$=3.66 min purity>98% by ELSD; Reporter IQR$_3$: HPLC t$_R$=4.01 min; MALDI: [M+H]$^+$ 1741.36; HRMS (ESI)$^+$ m/z: Calcd for C$_{101}$H$_{117}$N$_{11}$O$_{16}$ ([M+3H]/3)$^+$ 581.2977. Found 581.3067; IR (neat) v (cm$^{-1}$): 1588.8, 1414.8, 1337.3, 1178.3, 1131.9, 683.5.

Cell Isolation and Culture

Human peripheral blood leukocytes from healthy volunteers were prepared as previously described[25]. Briefly, citrated blood was centrifuged at room temperature for 20 min at 350 g, and platelet-rich plasma was removed. Autologous serum was prepared by recalcification of platelet-rich plasma by addition of CaCl$_2$ to a final concentration of 2 mM. Leukocytes were separated from erythrocytes by dextran sedimentation using 0.6% dextran T500 (Pharmacia, Milton Keynes, UK), and the leukocyte-rich upper layer was then fractionated using isotonic Percoll (Pharmacia). Neutrophils and mononuclear leukocytes (PBMC) were harvested from the 68%|81% and 55/68% interfaces, respectively. In some experiments, neutrophils were labelled with DiD (Invitrogen, molecular probes) (2.5 µM) in D-PBS (w/o Ca/Mg) for 20 min at room temperature.

PBMC-derived macrophages were generated from mononuclear leukocytes as follows (Rossi A G, McCutcheon J C, Roy N, Chilvers E R, Haslett C, Dransfield I. Regulation of macrophage phagocytosis of apoptotic cells by cAMP. *J Immunol.* 1998 Apr. 1; 160(7):3562-8. Regulation of macrophage phagocytosis of apoptotic cells by cAMP). Mononuclear leukocytes were allowed to adhere to poly-d-lysine coated coverslips for 1 hour before washing to remove non-adherent cells. Adherent cells were cultured for 7-10 days in vitro (DIV) in IMDM containing 10% autologous serum.

A549 cells (ATCC CCL-185) were maintained at 80-90% confluence in culture medium which consisted of Dulbecco's modified Eagle's medium (4.5 g·l$^{-1}$ glucose) supplemented with 10% (v/v) heat inactivated fetal calf serum (FCS), L-glutamine (2 mM), streptomycin (50 µg·ml$^{-1}$) and penicillin (50 units·ml$^{-1}$) in a thermostatted (37° C.) and humidified atmosphere of 5% CO$_2$/95% air. Suspensions of exponentially growing cells (2×10$^6$ cells), detached following trypsin/EDTA exposure were then seeded onto coverslips or 6 well microplates and grown to confluence over 24-48 h.

Bronchoalveolar lavage (BAL) was obtained from patients with Idiopathic Pulmonary Fibrosis (IPF). Written informed consent was obtained from all subjects. The study was approved by the Lothian Research Ethics Committee. BAL was performed as part of ongoing clinical research studies. 200 ml of saline was instilled into the right middle lobe and lavaged in 20 ml aliquots. Samples were kept on ice and 100 µl aliquots pipetted onto coverslips followed by immediate staining as detailed and live confocal imaging in a POC mini (perfusion open and closed) (PeCon GmbH) cultivation chamber.

Live Cell Imaging and Staining for Confocal Microscopy

A laser-scanning confocal imaging system (LSM510; Carl Zeiss, Jena, Germany), incorporating an upright Axioskop FS2 microscope (63× objective) was used for image acquisition and processing. Exposure to 488 nm light was limited to 1-6% of the maximum laser power in order to minimize photobleaching and toxicity. In all cases, images were obtained without Kalman averaging and typically with a pixel dwell time of 3.2 µs with a pinhole diameter corresponding to 1 Airy unit. In multiple-labelling experiments pinhole diameters were adjusted to give optical Z-sections of equivalent depths, corresponding to 1 Airy unit for the longest excitation wavelength. All live time-lapse imaging of was performed in IMDM. Coverslips were transferred to a thermostatted environmental stage (POC Mini) maintained at 30° C.[26]. Drugs were added by bath addition. In experiments where fluorescein was examined alone, the fluorophore was excited with a dedicated 488 nm line, and emitted light reflected from a NFT545 filter and passed through an LP505 filter.

In multiple labelling experiments involving membrane (DiD, Invitrogen), or dextran-647, and IQR probes, images were obtained simultaneously. DiD or dextran-647 was excited with a dedicated 633 nm line, and emitted light detected with meta detector (650-705 nm), whereas Fluorescein was excited with a dedicated 488 nm line, and emitted light reflected from a NFT545 filter and passed through an LP505 filter.

In multiple labelling experiments using IQR probes in combination with syto-85 (Invitrogen, 2.5 µM, 30 minutes, 37° C.), images were acquired sequentially. Fluorescein was excited with a dedicated 488 nm line and emitted light reflected from a NFT545 filter and passed through an LP505 filter whereas syto-85 were excited with a dedicated 543 nm line, and emitted light detected with meta detector (575-695 nM).

Time-Course Experiments of Cell Activation

Neutrophils and mononuclear cells (6×10$^6$ cells total), or PBMC-derived macrophages, were seeded onto glass coverslips pre-coated with 10 µg/ml fibronectin (Sigma). Cells were allowed to adhere and 10 µM (final concentration) IQR1.2 added to wells prior to transfer to POC mini and placement in environmental chamber. Live imaging commenced at 30 s intervals. Baseline images were acquired for 10-15 min prior to addition of A21387 (10 µM, Sigma) and live time-lapse confocal images acquired for further 20 min. Where sivelestat or dynasore was included, cells were pretreated for 10 minutes prior to imaging.

A549 Epithelial Cell/Activated Neutrophils Overnight Coculture

A549 cells grown to confluence (>80%) in 6 well plates on coverslips were used and cultured as described above. Coverslips were transferred to POC mini and freshly isolated neutrophils added (0.6–1.2×10$^6$). The coculture was allowed to settle for 30 min prior to addition of PAF (platelet activating factor) (10 nM, Sigma) for 5 min then fMLP (formyl-met-leu-phe)(10 nM, Sigma) (1.8 mM calcium). For these experiments IQR was present throughout at 1 µM. Z-stack images for 3D reconstruction were captured every 15 min overnight for 15 h.

Images for Deconvolution.

Images were acquired at the correct Nyquist sampling rate. Scanning area was reduced to minimum to allow quicker scanning times per z-section. Images were deconvolved using Hyugens Essential (1000 iterations maximum).

Murine Experiments

To induce lipopolysaccharide (LPS) lung inflammation, methods as detailed previously were used[27]. Briefly, LPS (10 ug/mouse *E. coli* LPS) was instilled by direct intubation to induce a neutrophilic alveolitis. 24 hours later, BAL was obtained after euthanasia of mice with 800 ul aliquots of ice cold PBS into the exposed and intubated murine trachea on three occasions.

Fluorescent Microplate Reader Experiments

IQR4 (0.5 uM) was incubated with of human neutrophil elastase (HNE; 11.3 ug/ml) in reaction buffer (50 mm Hepes buffer, pH 7.4, 0.75 m NaCl, 0.05% Igepal CA-630 (v/v)) with or without of sivelestat (50 uM). The timecourse of fluorescence dequenching was followed for 30 min with a fluorescence microplate reader (excitation 480/20, emission 528/25). A fluorescence increase is observed only in presence of HNE, and this is inhibited by the presence of sivelestat.

For experiments using neutrophil lysate, IQR4 (0.5 uM) is incubated with freeze-thawed neutrophil lysate (10×10$^6$ cells/ml) in IMDM with or without sivelestat (50 uM). The timecourse of fluorescence dequenching was followed for 30 min with a fluorescence microplate reader (excitation 480/20, emission 528/25).

In Vitro Cellvizio Experiments

Human neutrophils were isolated as described above and suspended in PBS with or without activating agents. A fibreoptic confocal system (488 Cellvizio) was used to acquire images in eppendorfs of cells both in the presence of free FAM and IQRs and after washing cells of free FAM and IQR in media. Imaging was performed for 60 s and representative still frames converted to bmp format.

In Vivo Cellvizio Experiments

Commercially available sheep were purchased. Sheep were sedated, intubated and ventilated. Cells: neutrophils, activated neutrophils, and activated monocytes were instilled (5 million in 5 ml) into disparate ovine subsegments via direct visualisation (under bronchoscopy) to the 3$^{rd}$ order bronchi and then a microcatheter was instilled into the working channel and the cells were visualised. As a control, 5 mls of IQR 2.2 was also insilled into a subsegment. Following this the microcatheter was replaced and 2 ml of 5 μm concentration of IQR2.2 was instilled 5 min later into the designated subsegments. Five minutes later, alveoscopy was performed by passing a alveofiex (fibreoptic bundle) down the working channel and live imaging commenced upon distal alveoscopy. Images were captured at 12 frames per second and representative frames converted to jpeg format.

Ex Vivo Cellvizio Experiments

An ex vivo ovine lung was ventilated and perfused with human blood (10% haematocrit). Following this, a bronchoscope was used to instill 500 mcg of *E. coli* LPS into the upper right segment. PBS as control was instilled into the upper left segment. 6 hours later, IQR1.2 was instilled (10 mcg) into each segment and probe based confocal laser endomicroscopy was performed with immediate imaging.

Experimental for the Synthesis of IQR4

Structure of Probe IQR4

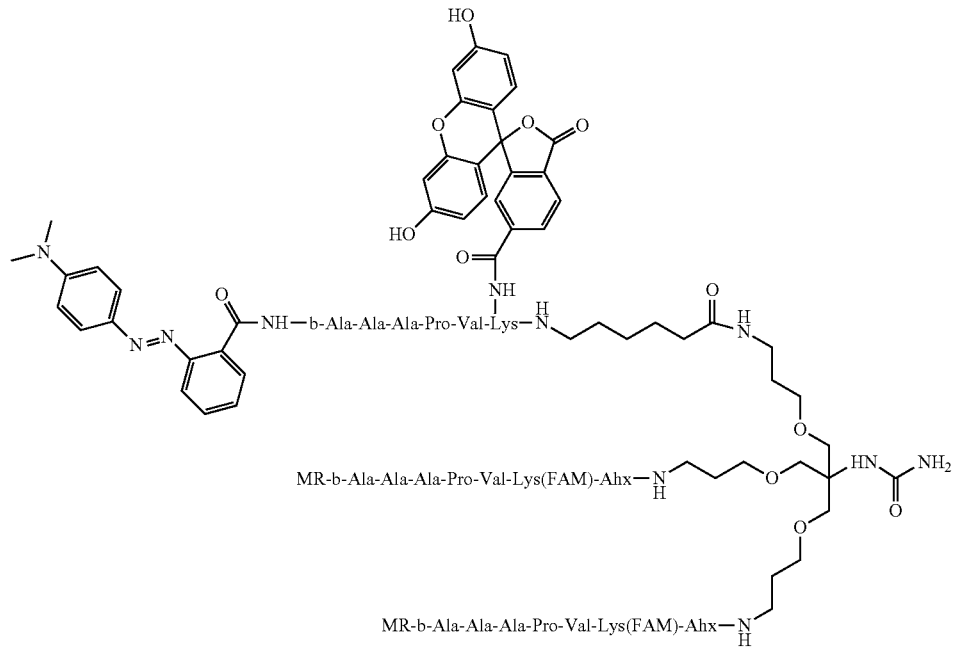

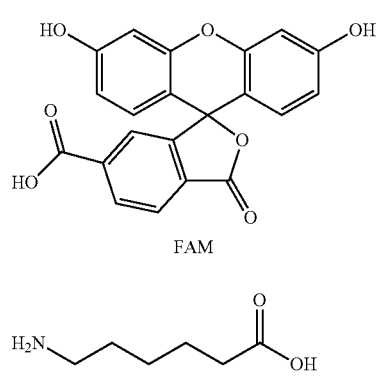

Chemical Formula: $C_{215}H_{264}N_{38}O_{46}$
Molecular Weight: 4116.62

35

Outline of the Synthesis:
1) Preparation of the monomer,
2) Preparation of Fmoc-Lys(Dde)-OH,
3) Attaching the monomer to PS resin,
4) Solid-phase synthesis,
5) Cleave from the resin,
6) Purification by HPLC.

General Information:

All amino acids, Aminomethyl Polystyrene Resin (1.23 mmol/g, 100-200 mesh, 1% DVB) and Rink Amide Linker were purchased from GL Biochem (Shangai) Ltd and NovaBiochem. 5(6)-carboxyfluorescein was from NovaBiochem and Oxyma from Apollo Scientific.

The Synthesis of Monomer (6) is Described in Previous Session (Page 20)

Synthesis of Fmoc-Lys(Dde)-OH

Fmoc-Lys(Dde)-OH is prepared in 3 steps

Scheme 1: Synthesis of Fmoc-Lys(Dde)-OH

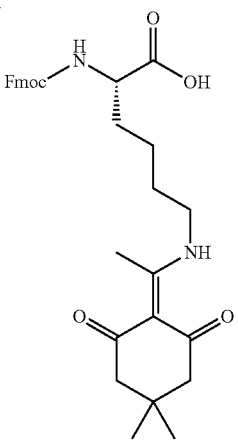

Synthesis of Dde-OH

Dimedone (21.2 g, 151 mmol, 1 eq), 4-(Dimethylamino)pyridine (DMAP, 19.0 g, 156 mmol, 1.05 eq) and 1-(3-Dimethylaminopropyl)-3-ethylcarbodiimide hydrochloride (EDCl.HCl, 29.1 g, 152 mmol, 1.05 eq) were dissolved in DMF (145 mL). Acetic acid (8.5 mL, 148 mmol, 1.05 eq) was added and the reaction was stirred overnight. The DMF was removed in vacuo, the residue was dissolved in EtOAc (150 mL) and washed with 1M HCl (2×200 mL) and water (2×200 mL). The organic phase was dried over MgSO$_4$, filtered, concentrated and dried in vacuo to give a yellowish solid (22.4 g, 83%), which was used without further purification. (Ref: *Org. Let.*, 2008, 10(10), 2015).

Synthesis of Fmoc-Lys(Dde)-OH

Fmoc-Lys-OH.HCl (10.2 g, 25.2 mmol) was dissolved in H$_2$O, N,N-diisopropylethylamine (DIPEA 1.1 eq, 4.8 mL, 27.7 mmol) was added and the resulting solid was collected by filtration and dried in a vacuum oven overnight. To a stirred suspension of Fmoc-Lys-OH (7.9 g, 21.4 mmol, 1 eq) in ethanol (250 mL), Dde-OH (7.8 g, 42.8 mmol, 2 eq) and TFA (160 µL, 2.14 mmol, 0.1 eq) were added. The reaction was refluxed for 60 hours. After the reaction mixture was cooled to room temperature, the solvent was removed in vacuo and the residue was dissolved in EtOAc (300 mL), washed with 1M KHSO$_4$ (2×200 mL) and 1M HCl (2×200 mL). The organic phase was dried over MgSO$_4$, filtered, and evaporated in vacuo. Fmoc-Lys(Dde)-OH was isolated by flash column chromatography (elute with 10% acetic acid/ethyl acetate) and crystallised from ethyl acetate/hexane as an off white solid (7.5 g, 70%).

Solid Phase Peptide Synthesis

Peptide coupling based on Fmoc deprotection strategy using solid support.

Peptide sequence: H-βAla-Ala-Ala-Pro-Val-Lys-

Scheme 2: Solid Phase synthesis

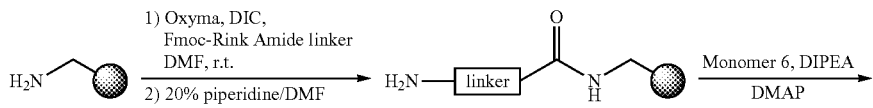

-continued

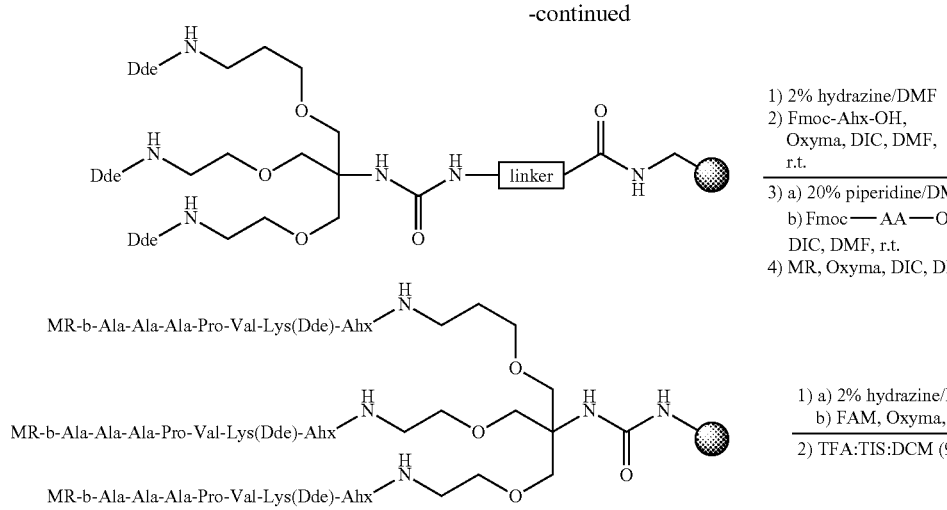

Fmoc-Rink Amide-PS resin was prepared using a 4-[(2,4-dimethoxyphenyl)-(Fmoc-amino)methyl]phenoxyacetic acid (Rink amide linker) attached to aminomethyl PS resin (1.23 mmol/g, 1% DVB, 100-200 mesh). Thus Fmoc-Rink-amide linker (3 eq) was dissolved in DMF (0.1M) and Oxyma (3 eq) was added and the mixture was stirred for 10 min. DIC (3 eq) was then added and the resulting mixture was stirred for further 5 min. The solution was added to aminomethyl polystyrene resin (1 eq) and shaken for 2 hours. The resulting resin was washed with DMF (3×10 mL), DCM (3×10 mL) and MeOH (3×10 mL).

After the tri-branched monomer was attached using DIPEA/DMAP at r.t. overnight (Tet. 2003, 59, 3945). 2% hydrazine in DMF solution was used (×2) for 1.5 h to deprotect the Dde-group.

All Fmoc deprotections are carried out with 20% piperidine in DMF for 10 min. The solution was then drained and the resin was washed with DMF (3×10 mL), DCM (3×10 mL) and MeOH (3×10 mL). This procedure was repeated twice. The deprotection was monitored by the Kaiser test (primary amines) and the chloranil test for secondary amines.

Solid Phase Couplings:

A solution of the appropriate Fmoc-amino acid or Methyl red (MR) or 5(6)-carboxyfluorescein (FAM) (10 eq) and Oxyma (10 eq) in DMF (0.1M) was stirred for 10 min. DIC (10 eq) was then added and the resulting solution was stirred for further 5 min. The solution was then added to the resin (1 eq), pre-swollen in DCM (10 mL), and the reaction mixture was shaken for 6 hours. The solution was drained and the resin washed DMF (3×20 mL), DCM (3×20 mL) and MeOH (3×20 mL). The coupling reactions were monitored by the Kaiser and chloranil tests.

After the FAM coupling the resin was washed with 20% piperidine to remove any fluorescein phenol esters.

The probe was then released from the resin using a cocktail of TFA/TIS/DCM (90/5/5) for 3 h. To the filtrate, cold ether was added to precipitate the product.

Purification of Probe IQR4

Initial purification was done by ether precipitation. Cold ether was added and collected by centrifugation. Washing was repeated with cold ether 4 times.

Purification of the probe was performed on a RP-HPLC (HP1100) system equipped with a Discovery C18 reverse-phase column (250×4.6 mm, 5 µm) with a flow rate 1 mL/min and eluting with 0.1% HCOOH in $H_2O$ (A) and 0.1% HCOOH in $CH_3CN$ (B), with a gradient of 5 to 95% B over 25 min and an initial isocratic period of 2 min ($t_r$=21.2 min).

Analysis of the probe was performed on a RP-HPLC (HP1260) system equipped with a Discovery C18 reverse-phase column (50×4.6 mm, 5 µm) with a flow rate 1 mL/min and eluting with 0.1% HCOOH in $H_2O$ (A) and 0.1% HCOOH in $CH_3CN$ (B), with a gradient of 5 to 95% B over 13 min and an initial isocratic period of 2 min ($t_r$=9.45 min).

Results

Figure 1:
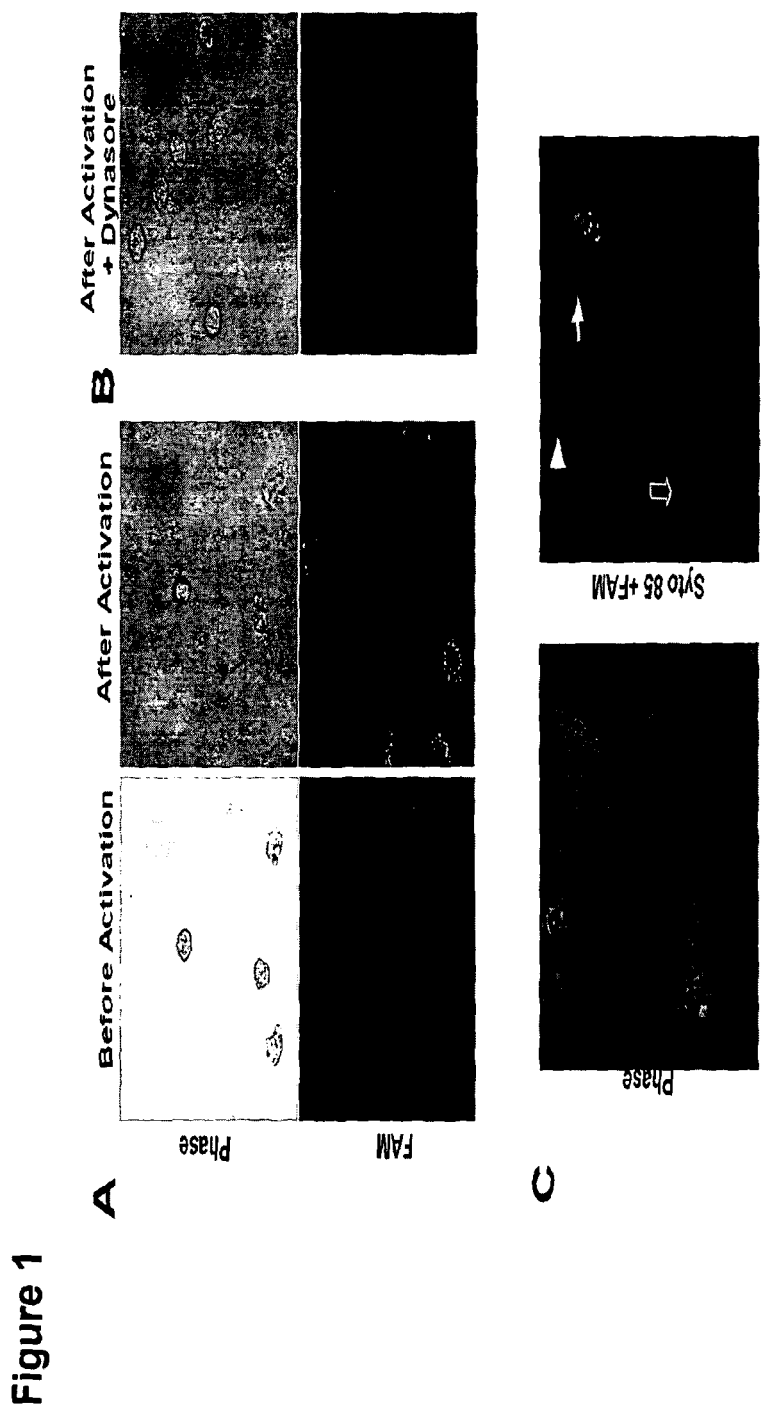
FIG. 1 shows live time-lapse confocal imaging of FAM uptake by primary human cells.

Fluid Phase Fluorophores Permit Detection of Cell Specific Uptake/Internalisation In Activated Neutrophils Using a Bench Top Confocal Initially we exposed quiescent and activated human neutrophils to a series of fluorophores and demonstrated the activation dependent uptake of fluorophores in human neutrophils. Only activated neutrophils or permeabilised neutrophils bound dye in a punctuate manner. Neutrophils were imaged continuously in the presence of the fluorophores (FIG. 1). The active uptake of the fluorophores was inhibited by the presence of a dynamin inhibitory agent (FIG. 1) showing that this process was dynamin dependent. Importantly, monocytes and lymphocytes did not take up the dyes.

IQR Specifically Dequenches in Neutrophils Compared to Other Highly Pinocytic/endocytic Cells Such as Human Macrophages Having demonstrated high levels of endocytosis in neutrophils and cells such as macrophages. We applied IQR1 to macrophages and demonstrated no dequenching or fluorescent amplification of IQR1. This demonstrates that a closely related cell to neutrophils shows absolutely no dequenching despite having a high endocytic rate (FIG. 14).

Internally Quenched Dendrimeric Reporters Permit Enhanced Signal to Noise Ratio And Detection of Uptake/Internalisation on Benchtop Confocal Having demonstrated the neutrophil specific staining by these dyes, we wished to optimise the profiles of the optical detection of neutrophil activation to permit high signal-to-noise ratios. In that regard, we and (more recently) others have shown that multivalent fluorescent peptide dendrimers, display the phenomenon of internal fluorescence quenching[18,28]. Dendrimers possess unique molecular architectures and dimensions compared to traditional linear polymers, are monodisperse, easy to synthesize and their sizes can be accurately controlled[15]. Additionally their biocompatibility, low toxicity and important ability to access the intracellular compartment[29,30], supports their use as scaffolds for permitting fluorophore quenching and hence as potential 'smart' visualisable sensors of neutrophil activation as their quenching may inherently permit high signal to noise discrimination in the inflammatory milieu. Using carboxyfluorescein (FAM) or rhodamine (TAMRA) as exemplar fluorophores, we hypothesised that placing dyes spatially orientated as dendrimeric internally quenched reporters (IQRs) would generate neutrophil activation probes with high signal to noise ratios. Conceptually, the delivery of these probes to the inflammatory milieu would permit sufficient pericellular quenching to readily visualise individual cells which had undergone activation dependent accumulation of dyes. Hence alongside monomeric fluorophore, we synthesised dendrimers with three and six branches, called respectively IQR1 and IQR2 (FIG. 2). As the FAM dendrimer displayed a brighter signal in vitro and as the fibreoptic confocal device used in this study was aligned to this wavelength, the FAM dendrimer was chosen to develop the other compounds instead of rhodamine. Initial studies showed that these structures permitted the detection of neutrophil uptake/internalisation (conformed by colocalisation with fluorescently conjugated dextran) (FIG. 3). Again these structures permitted the cell specific detection of uptake/internalisation (FIG. 3).

Dendrimeric IQRs but not FRET IQRs with Enhanced Solubility Permit Cell Specific Detection For the ultimate delivery of these optical reporters to the human lung, they would require enhanced solubility compared to the probes described above. Hence the enhanced solubility of these IQRs was achieved by incorporating a small series of peptides within the dendrimer backbone (IQR1.2 and IQR2.2) or pegylating the probes (IQR1.3 and IQR2.3) (FIG. 4). As above, these were initially evaluated in vitro for selectivity against other cells commonly obtained from the inflammatory milieu; monocytes, macrophages and lymphocytes and epithelial cells. Again, we confirmed the cellular specificity of the probes using live confocal imaging (FIG. 5). This was extended to freshly isolated cells from the SAL of patients with IPF. SAL analysis revealed a mixed inflammatory infiltrate, but again with only neutrophils activating the dendrimeric probe scaffold both before and after stimulation (FIG. 6). Co-cultures of neutrophils and epithelial cells demonstrated that no probe activation occurred on epithelial cells despite 24 h of exposure of epithelial cells to IQRs (FIG. 7) Additionally and surprisingly, this activation dependent labelling was species specific (FIG. 8).

Importantly, using an alternative structural strategy to produce an IQR, FRET probes did not permit direct visualisation of cell uptake, but this remains unexplained. (see FIG. 9). Thus, these dendrimeric IQRs provide an optimised tool to directly assess neutrophil activation status in freshly isolated biological samples providing enhanced signal to noise ratios.

Experiments were then performed to ascertain dynamic activation in cells with the soluble dendrimeric reporters using live time-lapse confocal microscopy as performed using the monomeric dyes. Freshly isolated human neutrophils were continuously imaged before and immediately after stimulation (FIG. 10) and demonstrated a striking, rapid increase in cell-associated fluorescence (FIG. 10b). To determine the precise cellular localization of fluorescence, live high resolution multi-stack images were acquired after stimulation of neutrophils. These showed prominent perimembranous activity alongside intracellular activation (FIG. 10c). This colocalized with fluorescent dextran confirming uptake by pinocytosis and again was dynamin dependent.

We compared the non-dendrimeric FAM, with the branched dendrimers of the present invention. As the dendrimer branches increased in number, the quenching increased as expected leading to an increase in the signal to noise ratio obtainable.

IQR Fluorescent Amplification in Neutrophils is Dependent on the Combination of Endocytosis and Degranulation.

We performed experiments utilising latruniculin (actin cytoskeleton inhibitor) that showed increased amplification of fluorescence. These indicated that the IQR neutrophil specific signal may be affected by actin cytosleton rearrangements during the process of cell activation. We assume that the dequencing is due to the combination of endocytosis and degranulation. As such we tested key components of the neutrophil granule against IQR. No differences were seen with myeloperoxidase inhibitors, reactive oxygen species. The conclusion drawn was that the probes of the present invention requires both degranulation and also endocytosis.

The Solubilsed Dendrimeric IQRs Exhibit No In Vitro or In Vivo Toxicity

Fundamental to applying the direct delivery of these probes for human clinical use, was the requirement to demonstrate no toxicity and in particular no pulmonary toxicity when delivered directly in to the lung. No cellular toxicity was observed in any of the cells we used (FIG. 11). Additionally no pulmonary inflammatory response ensued upon direct intratracheal administration of milligrams of probe/kg to mice (FIG. 11).

In Vitro and In Vivo Experiments Using Fibreoptic Confocal Confirms the Potential Utility of Using the Probes for Detecting Activated Neutrophils To develop a methodology for detecting activated neutrophils deep within lungs and in particular the alveolar space of humans in the future, it was imperative that we utilise a size relevant model. In that regard the ovine lung provided a potential model[31] system to assess the spatiotemporal visualization of activated human neutrophils. We used a strategy employing fibred confocal microendoscopy. This permits cellular resolution at the alveolar level in both humans and animals. Initial characterisation was performed with the Cellvizio fibres in eppendorfs. This clearly demonstrated superior quenching of the 6 branch, IQR 2.3, with excellent signal to noise ratios (FIG. 12). In particular that single free dyes that have previously been used to image pinocytosis would not permit such visualisation with fibreoptic confocal (FIG. 12). Subsequently, human neutrophils were delivered by microcatheter into a defined subsegment of the ovine lung. Subsequently a minute quantity of IQR was instilled in the same segment (44 µg). Confocal microendocscopy with Cellvzio 488 was performed in control segments (pre delivery of activated monocytes, quiescent neutrophils and probe alone) and were compared with imaging in segments that had received activated neutrophils (FIG. 13). Only segments that had received activated neutrophils, clearly demonstrated fluorescent cells (FIG. 13).

Figure 15:
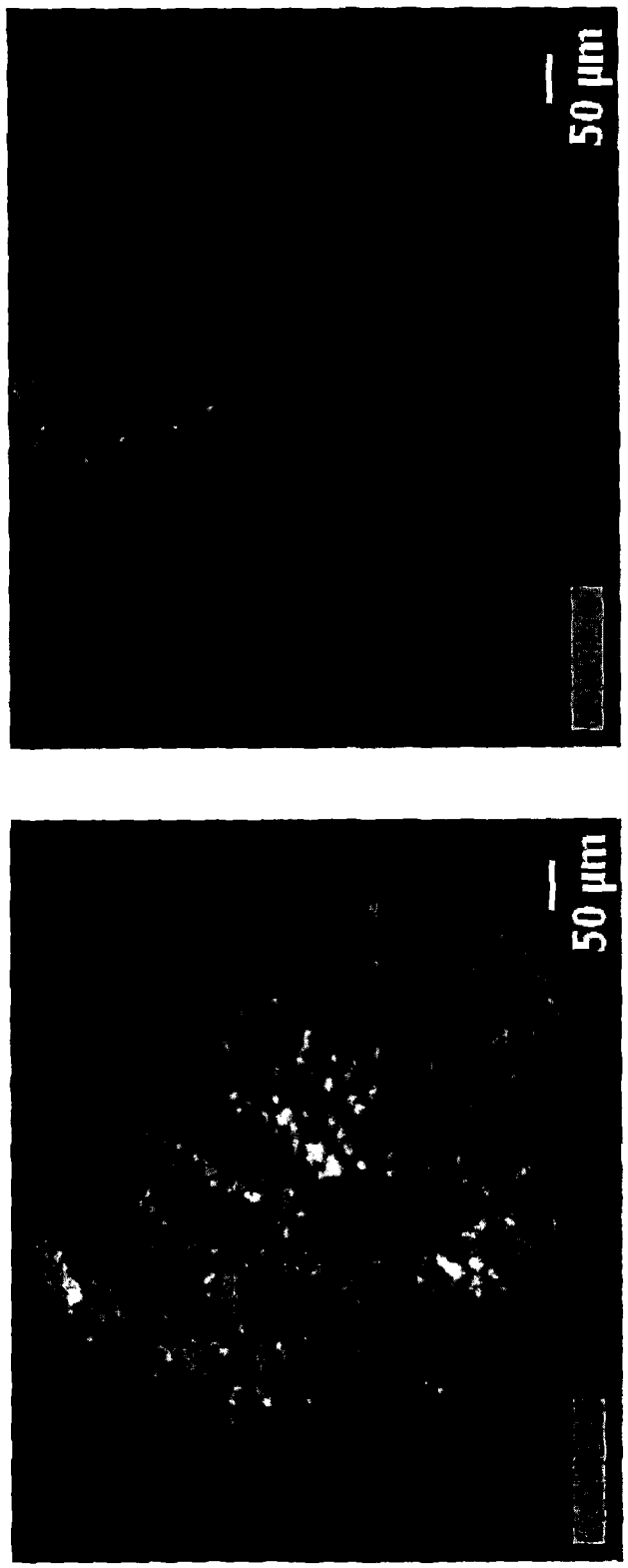

A further experiment (FIG. 15) was performed to image recruited activated human neutrophils. In this experiment, an ex vivo ovine lung was ventilated and perfused with human blood. Following this, a subsegment of the lung received lipopolysaccharide to induce the recruitment of human neutrophils. 10 µgγ of IQR1.2 was delivered into a control segment and the LPS instilled segment. Only the LPS segment showed signal enhancement imaged using probe based confocal microendoscopy. This experiment conclusively demonstrated that recruited activated neutrophils can be detected by IQR.

The method and timing of probe delivery are crucial to this approach. Only minute quantities are required (<100 µg) and the timing of detection is within minutes. To image differential neutrophil pinocytosis, it is imperative that imaging is conducted immediately as delaying imaging may lead to pinocytic uptake by other cells within a few hours. The directed delivery of minute quantities foregoes any toxicity issues and direct instillation into the distal lung is ideally suited to confocal microendoscopy to permit molecular resolution. Proof of concept in vivo is demonstrated.

In summary, directly visualisable reporters of neutrophil activity provide a potential diagnostic tool. Especially in the setting of neutrophil dominant conditions such as acute lung injury. Developing bedside methodologies could aid in stratifying those patients who have chest x-ray infiltrates due to non inflammatory causes versus those with either sterile or infective lung injury. Confocal laser microendoscopy coupled with the delivery of small concentrations of molecular probes permits the visualisation deep within the lung and provides the detection platform for the delivery and imaging of such probes in humans.

Figure 16:
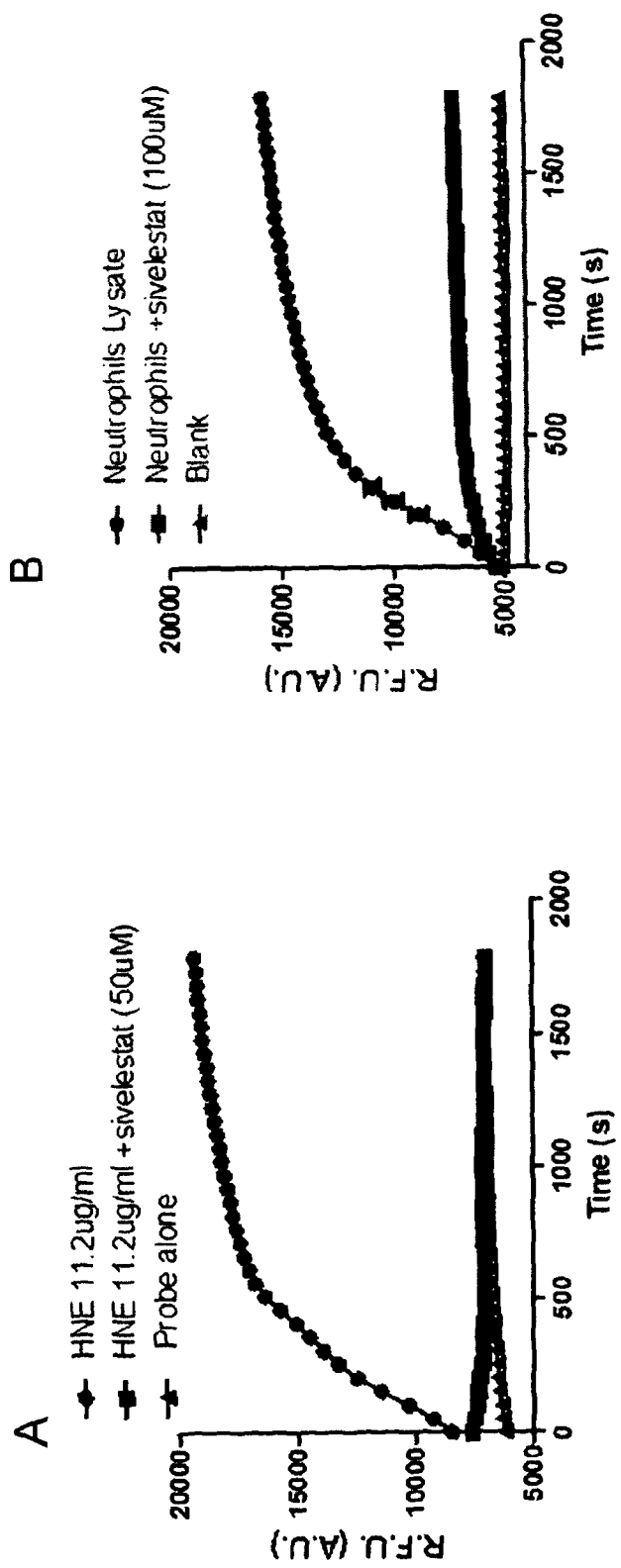
Figure 17:
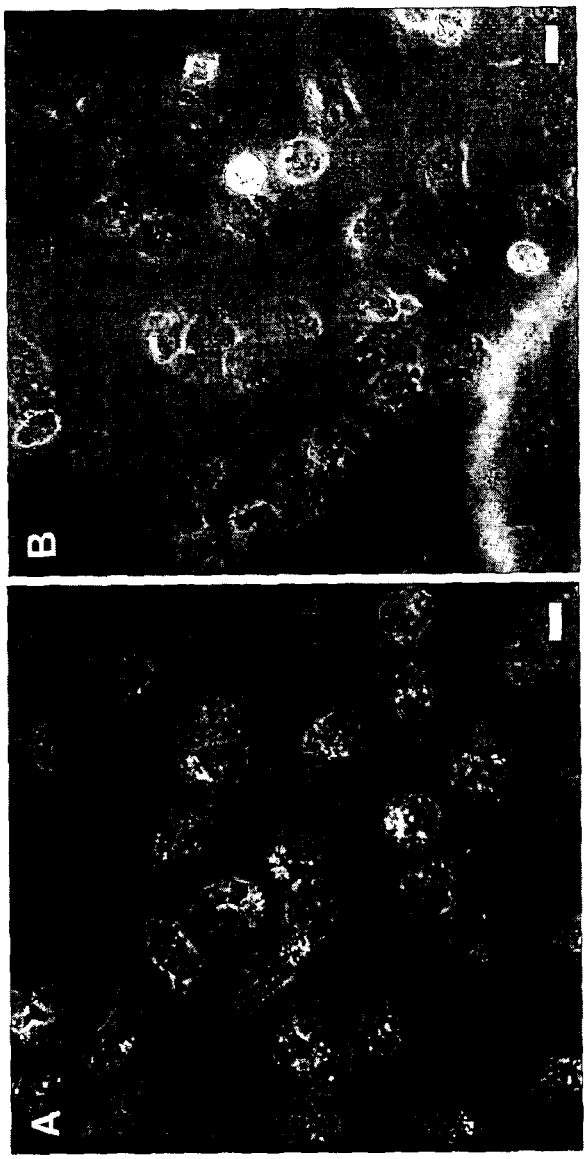

A dendrimeric IQR incorporating a FRET-based elastase reporter was generated and shown to be dequenched by recombinant HNE and neutrophil lysate, an effect that was blocked by the specific elastase inhibitor sivelestat (FIG. 16). Furthermore, in live confocal imaging experiments this FRET-dendrimer IQR construct reported elastase activity on neutrophils, since the fluorescent cell-associated signal could be blocked by sivelestat (FIG. 17). Since elastase activity cleaves the dark quencher moieties from the fluorophore/dendrimer scaffold, it is thought that the elastase-dependent labelling of neutrophils occurs by virtue of the degranulation-dependent signal exhibited by the non-FRET dendrimeric IQR's, following intra- or extracellular cleavage of the elastase-reporter peptide sequence and subsequent uptake/internalisation of the cleaved probe.

REFERENCES

[1] Balamayooran G, Batra S, Fessler M B, Happel K I, Jeyaseelan S., *Am J Respir Cell Mol Biol.* 2010, 43, 5.
[2] Tsushima K, King L S, Aggarwal N R, De Gorordo A, D'Alessio F R, Kubo K., *Intern Med.,* 2009, 48, 621.
[3] Conway M A, Kefala K, Wilkinson T S, Dhaliwal K, Farrell L, Walsh T, Mackenzie S J, Reid H, Davidson D J, Haslett C, Rossi A G, Sallenave J M, Simpson A J, *Am J Respir Crit. Care Med,* 2009, 180, 19.
[4] Pentz S, Horler H, *J Microsc,* 1992, 167, 97.
[5] Simpson A J, Wallace W A, Marsden M E, Govan J R, Porteous D J, Haslett C, Sallenave J M, *J Immunol,* 2001, 167, 1778. Simpson A J, Wallace W A, Marsden M E, Govan J R, Porteous D J, Haslett C, Sallenave J M, *J Immunol,* 2001, 167, 1778.
[6] den Hengst W A, Gielis J F, Lin J Y, Van Schil P E, De Windt L J, Moens A L, *Am J Physiol Heart Circ Physiol.,* 2010, 299, 1283.
[7] Abu-Amara M, Yang S Y, Tapuria N, Fuller B, Davidson B, Seifalian A., *Liver Transpl.* 2010, 16, 1016.
[8] Downey D G, Bell S C, Elborn J S, *Thorax.,* 2009, 64, 81.
[9] Demkow U, van Overveld F J, *Eur J Med. Res.,* 2010, 15, 27.
[10] Chen D L, Schuster D P, *Am J Physiol Lung Cell Mol Physiol.* 2004, 286, 834.
[11] Thiberville L, Salaün M, Lachkar S, Dominique S, Moreno-Swirc S, Vever-Bizet C, Bourg-Heckly G, *Proc Am Thorac Soc.* 2009, 6, 444.
[12] Thiberville L, Salaün M, Lachkar S, Dominique S, Moreno-Swirc S, Vever-Bizet C, Bourg-Heckly G, *Eur Respir J.* 2009, 33, 974.
[13] http://las.perkinelmer.com/Catalog/ProductInfoPage.htm?ProductID=NEV11169.
[14] Astruc D, Boisselier E, Ornelas C, *Chem. Rev.* 2010, 110, 1857.
[15] Biricova V, Laznickova A, *Bioorg. Chem.* 2009, 37, 185.
[16] Cummins W J, Hamilton A, Bradley M, Ellard J, Zollitsch T, Briggs M S J, 2003 Feb. 20, WO/2003/014743.
[17] Thiberville L, Moreno-Swirc S, Vercauteren T, Peltier E, Cave C, Bourg Heckly G. *Am J Respir Crit Care Med.* 2007, 175, 22.
[18] Ellard J M, Zollitsch T, Cummins W J, Hamilton A L, Bradley M, *Angew. Chem. Int. Ed Engl.,* 2002, 41, 3233.
[19] Lebreton S, How S E, Buchholz M, Yingyongnarongkul B E, Bradley M, *Tetrahedron,* 2003, 59, 3945.
[20] Knölker H J, Braxmeier T, Schlechtingen G, *Angew. Chem. Int. Ed.,* 1995, 34, 2497.
[21] O. Demmer, I. Dijkgraaf, M. Schottelius, H. J. Wester, H. Kessler, *Org. Let.,* 2008, 10, 2015.
[22] Brouwer A J, Mulders S J E, Liskamp R M J, *Eur. J. Org. Chem.* 2001, 1903.
[23] Kaiser E, Colescott R L, Bossinger C D, Cook P I, *Analytical Biochemistry,* 1970, 34, 595.
[24] Fischer R, Mader O, Jung G, Brock R, *Bioconjugate Chem.* 2003, 14, 653.
[25] Chua F, Laurent G J, *Proc. Am Thorac. Soc.* 2006, 3, 424.
[26] Donnelly S C, MacGregor I, Zamani A, Gordon M W, Robertson C E, Steedman D J, Little K, Haslett C, *Am J Respir. Crit Care Med.* 1995, 151, 1428.
[27] Shapiro S D, *Am J Respir. Cell Mol. Bio.1* 2002, 26, 266.
[28] Galande A K, Hilderbrand S A, Weissleder R, Tung C H, *J Med. Chem.* 2006, 49, 4715.
[29] Albertazzi L, Serresi M, Albanese A, Beltram F, *Mol. Pharm.* 2010, 7, 680.
[30] Najlah M. & D'Emanuele A, *Curr. Opin. Pharmacol.* 2006, 6, 522.
[31] Collie D D, MacAldowie C N, Pemberton A D, Woodall C J, McLean N, Hodgson C, Kennedy M W, Miller H R, *Clin Exp Allergy.* 2001, 31, 1636.

The invention claimed is:
1. A method of visualising a cell or cells within a mixture of cells in vivo using confocal fluorescence endomicroscopy, comprising the step of administering a dye construct to cells of a subject; and observing a cell or cells which have internalised the dye construct, by observing an increase in fluorescence by a factor of 1.2 or more from said cell or cells using a confocal endomicroscope; wherein
(a) the dye construct is a poly-branched molecule having any of the following generalized structures:

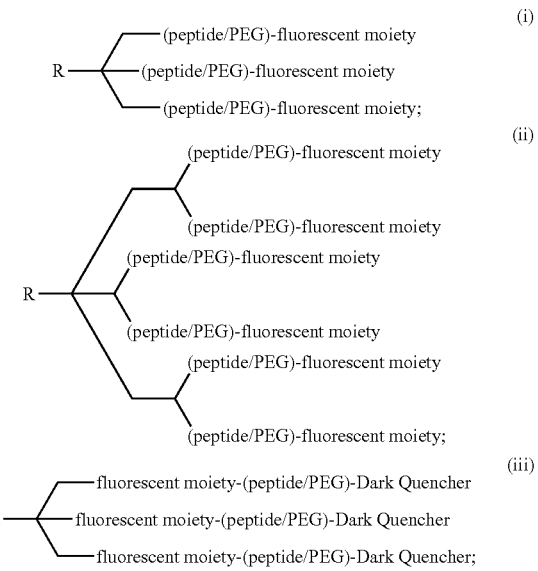

-continued (iv)
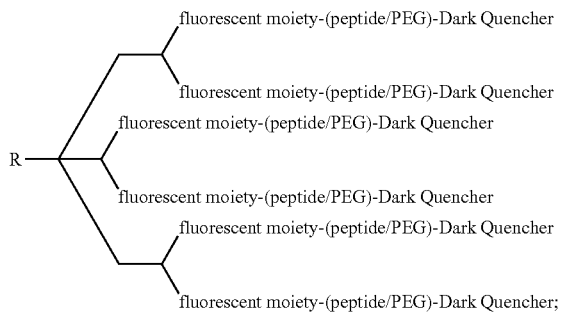

wherein R is selected from the group consisting of NH₂, CONH₂, an amino acid, OH, amino acid —CONH₂, CONH₂— amino acid, alkylamino, alkoxyamino, urea, thiol, carboxylic acid, or a fluorophore moiety which is the same or different from the fluorescent moieties of the poly-branched molecule of structure (i)-(iv) above, and wherein the R group is directly attached to the branch point, or is separated from the branch point by a spacer selected from the group consisting of a PEG group, or an alkyl or alkenyl chain; or (b) the dye construct is a poly-branched molecule selected from one of the following structures:

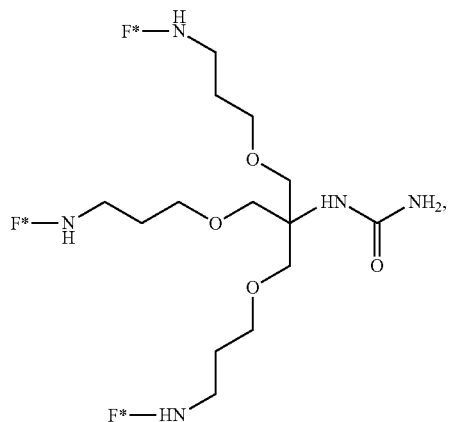

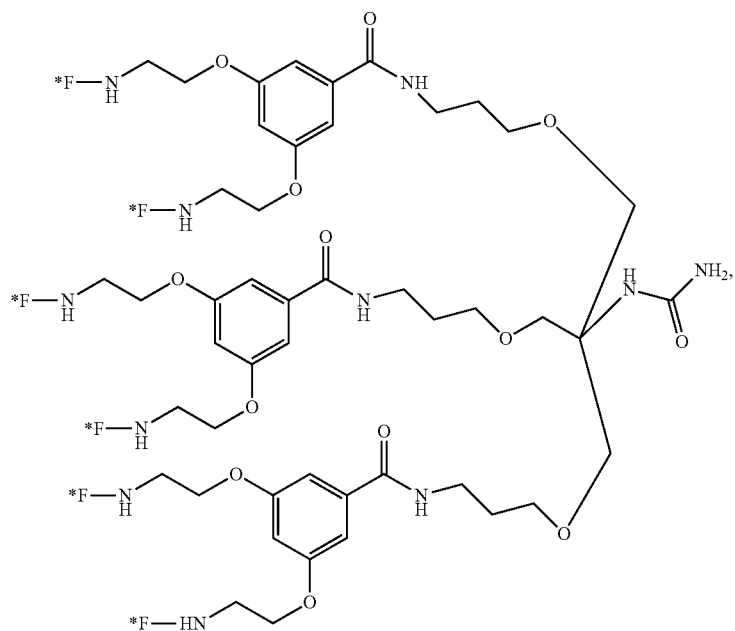

-continued
45
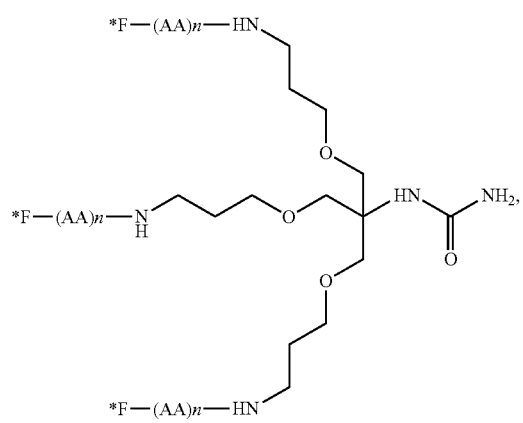
46
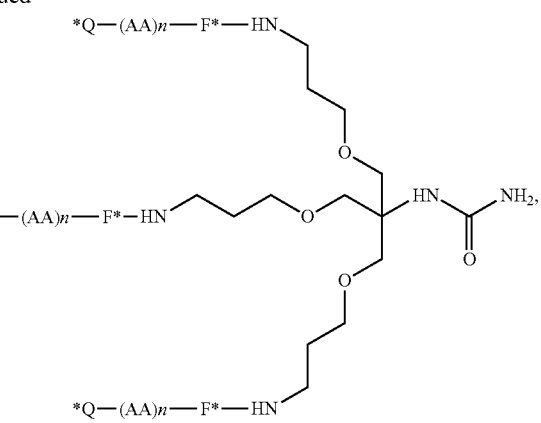
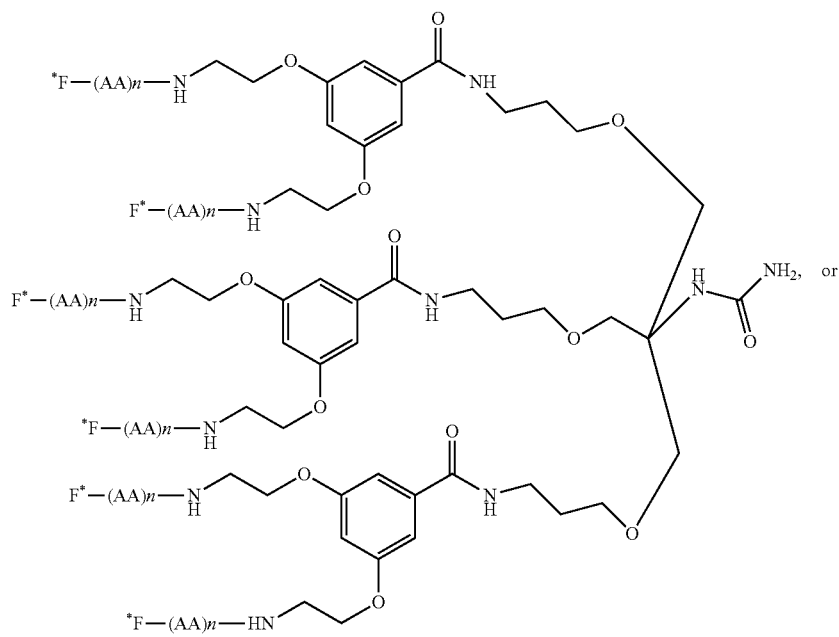, or
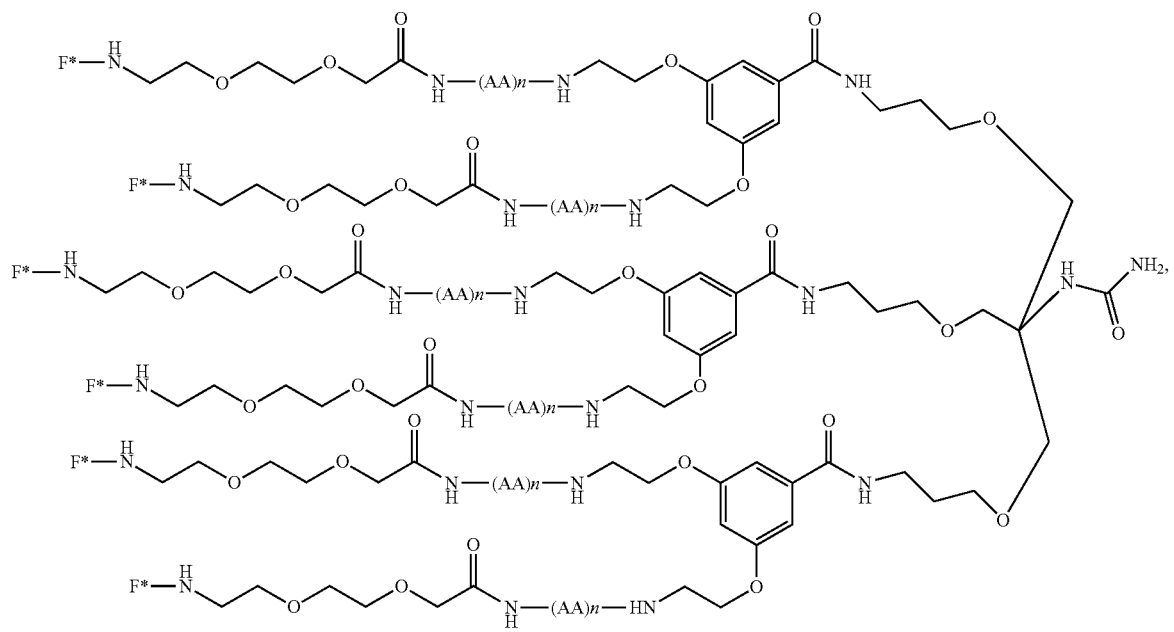

wherein (AA)n is absent or is present and wherein AA is any amino acid and n is a positive integer from 1 to 30; and wherein Q* is a dark quencher moiety and *F is a fluorescent moiety and wherein the dark quencher moiety Q* is independently selected from DABCYL, Methyl Red, BHQ1, BHQ2 and BHQ3.

2. The method according to claim 1 wherein the construct is to be administered locally and fluorescence is to be carried out in the gut; arteries and veins; the respiratory system, the brain; or the reproductive system.

3. The method according to claim 2, wherein the method is carried out in the lung.

4. The method according to claim 3 in order to detect activated neutrophils.

5. The method according to claim 1, wherein the fluorescent moiety *F is independently selected from FAM, rhodamine, a cyanine dye or a BODIPY dye.

6. The method according to claim 1 wherein the dye construct is locally administered to an area of tissue to be imaged.

7. The method according to claim 6 wherein detection of the cells which have internalized the dye construct is carried out within 1-30 min of the dye construct being administered to a subject.

8. The method according to claim 1 wherein the cell or cells to be detected are activated neutrophils.

9. The method according to claim 1 wherein the amount of the construct to be administered to a subject is less than 100 µg.

10. The method according to claim 1, wherein the dye construct is administered to the subject by a catheter inserted into the confocal endomicroscope.

11. A method of visualizing a cell or cells within a mixture of cells in vivo using confocal fluorescence endomicroscopy, comprising the step of administering a dye construct to cells of a subject, and observing fluorescence from said cell or cells using a confocal endomicroscope, wherein the dye construct is a poly-branched molecule selected from one of the following structures:

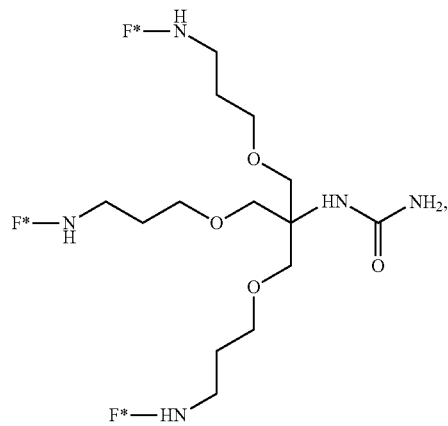

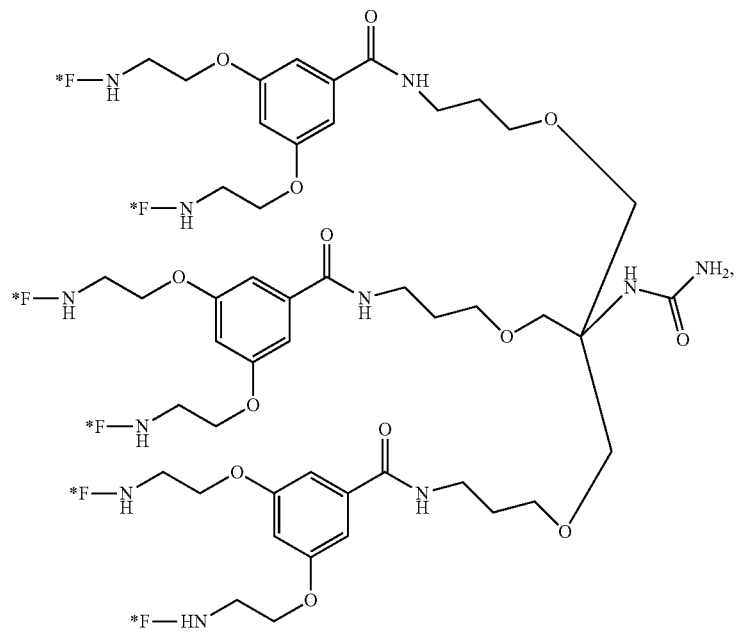

-continued
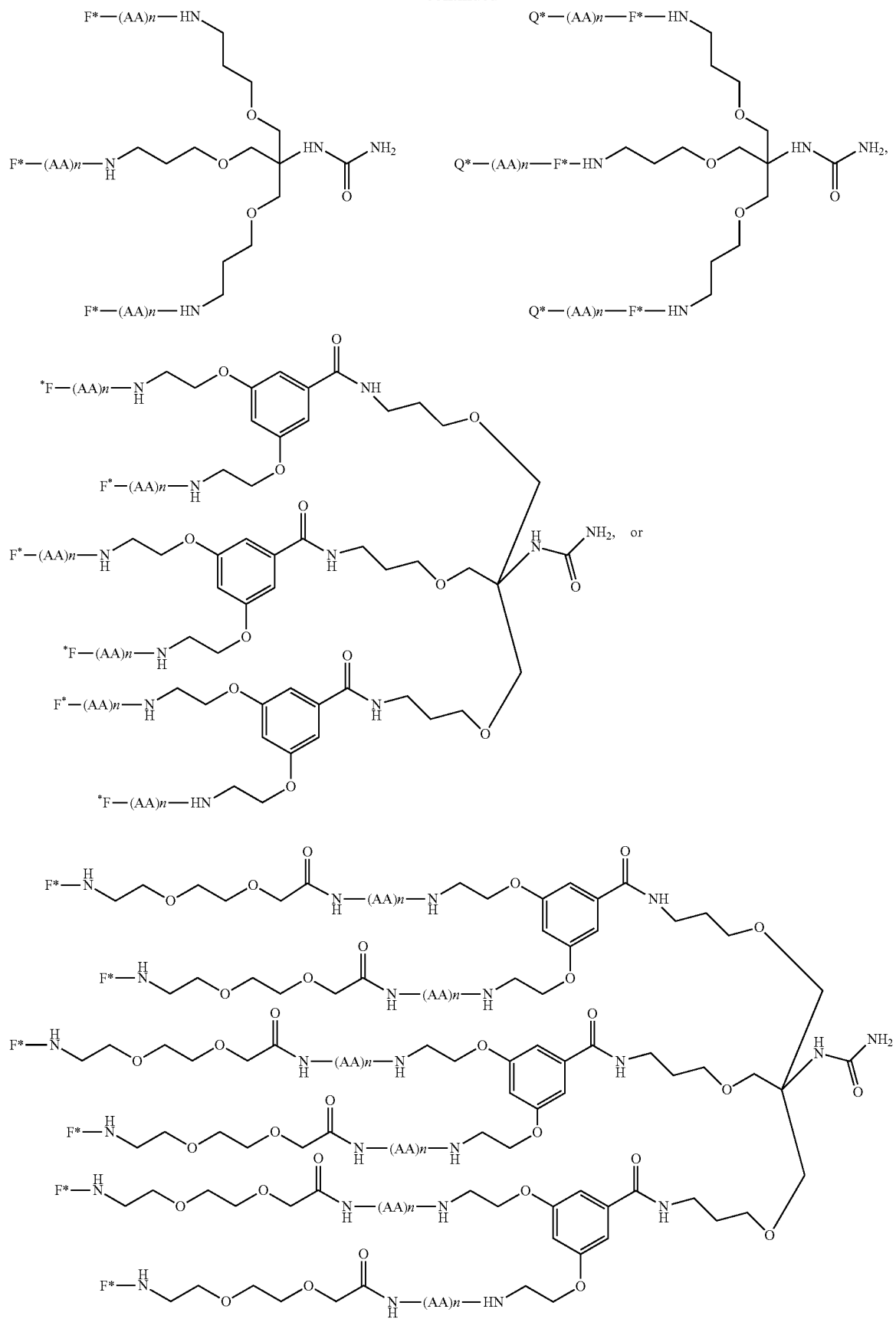

where (AA)n is optional and wherein when present AA is any amino acid and n is a positive integer from 1 to 30, and *F is independently selected from FAM, rhodamine, a cyanine dye or a BODIPY dye, and Q* is independently selected from DABCYL, Methyl Red, BHQ1, BHQ2 and BHQ3.

12. The method according to claim 11 wherein detection of the cells which have internalized the dye construct is carried out within 1-30 min of the dye construct being administered to a subject.

13. The method according to claim 11 wherein the cell or cells to be detected are activated neutrophils.

* * * * *